US011511110B2

(12) United States Patent
Wilkerson et al.

(10) Patent No.: US 11,511,110 B2
(45) Date of Patent: Nov. 29, 2022

(54) METHODS FOR TREATING URINARY STRESS INCONTINENCE

(71) Applicant: Viveve, Inc., Englewood, CO (US)

(72) Inventors: Deborah Wilkerson, Denver, CO (US); Stacie Bell, Lakewood, CO (US); Bruce Baldwin Allan, Calgary (CA)

(73) Assignee: VIVEVE, INC., Englewood, CO (US)

( * ) Notice: Subject to any disclaimer, the term of this patent is extended or adjusted under 35 U.S.C. 154(b) by 825 days.

(21) Appl. No.: 16/454,578

(22) Filed: Jun. 27, 2019

(65) Prior Publication Data

US 2020/0001079 A1 Jan. 2, 2020

Related U.S. Application Data

(60) Provisional application No. 62/690,534, filed on Jun. 27, 2018.

(51) Int. Cl.
*A61N 1/36* (2006.01)
*A61N 1/40* (2006.01)
*A61N 5/02* (2006.01)
*A61N 5/04* (2006.01)
*A61N 7/02* (2006.01)
(Continued)

(52) U.S. Cl.
CPC ......... *A61N 1/36007* (2013.01); *A61N 1/025* (2013.01); *A61N 1/403* (2013.01); *A61N 5/025* (2013.01); *A61N 5/045* (2013.01); *A61N 7/022* (2013.01); *A61N 1/0524* (2013.01); *A61N 2007/0004* (2013.01)

(58) Field of Classification Search
CPC ... A61B 18/04; A61B 18/12; A61B 2018/124; A61B 18/1206; A61B 18/14; A61B 18/08; A61B 18/082; A61N 1/0524; A61N 1/0521; A61N 1/0504; A61N 1/36007; A61N 1/36; A61N 5/022; A61N 5/025

See application file for complete search history.

(56) References Cited

U.S. PATENT DOCUMENTS 2,811,969 A 11/1957 Shubert
3,595,217 A 7/1971 Rheinfrank
(Continued)

FOREIGN PATENT DOCUMENTS

CN 2223112 Y 3/1996
CN 1241917 A 1/2000
(Continued)

OTHER PUBLICATIONS

Jul. 10, 2018 Office Action for TW106103270.
(Continued)

*Primary Examiner* — Jon Eric C Morales
(74) *Attorney, Agent, or Firm* — Michele V. Frank; Venable LLP

(57) ABSTRACT

Methods for treating urinary stress incontinence by non-invasively delivering energy to one or more submucosal regions of vaginal tissue to induce remodeling within the vaginal tissue are provided. In some embodiments, the energy delivery results in heating of the target tissue to a temperature that ranges from about 38° C. to about 46° C. In some embodiments, the subject methods involve cooling a mucosal epithelial layer over the vaginal tissue. In some embodiments, a reverse thermal gradient is produced as the mucosal epithelium is cooled while energy is delivered to the underlying vaginal tissue.

27 Claims, 7 Drawing Sheets

(51) Int. Cl.
*A61N 1/02* (2006.01)
*A61N 7/00* (2006.01)
*A61N 1/05* (2006.01)

(56) References Cited

U.S. PATENT DOCUMENTS

| | | |
|---|---|---|
| 3,741,211 A | 6/1973 | Vreeland, Jr. |
| 3,995,629 A | 12/1976 | Patel |
| 4,309,989 A | 1/1982 | Fahim |
| 4,326,529 A | 4/1982 | Doss et al. |
| 4,381,007 A | 4/1983 | Doss |
| 4,785,807 A | 11/1988 | Blanch |
| 4,785,828 A | 11/1988 | Maurer |
| 4,892,520 A | 1/1990 | Gilbaugh |
| 4,907,589 A | 3/1990 | Cosman |
| 4,920,978 A | 5/1990 | Colvin |
| 4,976,709 A | 12/1990 | Sand |
| 4,989,614 A | 2/1991 | Dejter, Jr. et al. |
| 5,010,895 A | 4/1991 | Maurer et al. |
| 5,046,511 A | 9/1991 | Maurer et al. |
| 5,143,063 A | 9/1992 | Fellner |
| 5,160,334 A | 11/1992 | Billings et al. |
| 5,230,349 A | 7/1993 | Langberg |
| 5,242,440 A | 9/1993 | Shippert |
| 5,301,692 A | 4/1994 | Knowlton |
| 5,330,469 A | 7/1994 | Fleenor |
| 5,334,193 A | 8/1994 | Nardella |
| 5,348,554 A | 9/1994 | Imran et al. |
| 5,403,311 A | 4/1995 | Abele et al. |
| 5,409,453 A | 4/1995 | Lundquist et al. |
| 5,443,470 A | 8/1995 | Stern et al. |
| 5,449,374 A | 9/1995 | Dunn et al. |
| 5,450,293 A | 9/1995 | Hoffman |
| 5,458,596 A | 10/1995 | Lax et al. |
| 5,469,857 A | 11/1995 | Laurent et al. |
| 5,569,242 A | 10/1996 | Lax et al. |
| 5,605,539 A | 2/1997 | Buelna et al. |
| 5,660,836 A | 8/1997 | Knowlton |
| 5,673,695 A | 10/1997 | McGee et al. |
| 5,755,753 A | 5/1998 | Knowlton |
| 5,765,567 A | 6/1998 | Knowlton |
| 5,807,392 A | 9/1998 | Eggers |
| 5,814,040 A | 9/1998 | Nelson et al. |
| 5,824,076 A | 10/1998 | Knowlton |
| 5,836,990 A | 11/1998 | Li |
| 5,871,524 A | 2/1999 | Knowlton |
| 5,893,849 A | 4/1999 | Weaver |
| 5,919,219 A | 7/1999 | Knowlton |
| 5,937,863 A | 8/1999 | Knowlton |
| 5,947,891 A | 9/1999 | Morrison |
| 5,948,011 A | 9/1999 | Knowlton |
| 5,951,550 A | 9/1999 | Shirley et al. |
| 5,954,717 A | 9/1999 | Behl et al. |
| 5,957,922 A | 9/1999 | Imran |
| 5,986,446 A | 11/1999 | Williamson |
| 6,002,968 A | 12/1999 | Edwards |
| 6,024,743 A | 2/2000 | Edwards |
| 6,035,238 A | 3/2000 | Ingle et al. |
| 6,044,847 A | 4/2000 | Carter et al. |
| 6,081,749 A | 6/2000 | Ingle et al. |
| 6,091,995 A | 7/2000 | Ingle et al. |
| 6,139,569 A | 10/2000 | Ingle et al. |
| 6,156,060 A | 12/2000 | Roy et al. |
| 6,216,704 B1 | 4/2001 | Ingle et al. |
| 6,236,891 B1 | 5/2001 | Ingle et al. |
| 6,241,753 B1 | 6/2001 | Knowlton |
| 6,277,116 B1 | 8/2001 | Utely et al. |
| 6,283,987 B1 | 9/2001 | Laird et al. |
| 6,292,700 B1 | 9/2001 | Morrison et al. |
| 6,311,090 B1 | 10/2001 | Knowlton |
| 6,322,584 B2 | 11/2001 | Ingle et al. |
| 6,350,276 B1 | 2/2002 | Knowlton |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,416,504 B2 | 7/2002 | Mosel et al. |
| 6,425,912 B1 | 7/2002 | Knowlton |
| 6,427,089 B1 | 7/2002 | Knowlton |
| 6,430,446 B1 | 8/2002 | Knowlton |
| 6,432,105 B1 | 8/2002 | Ellman et al. |
| 6,438,424 B1 | 8/2002 | Knowlton |
| 6,453,202 B1 | 9/2002 | Knowlton |
| 6,461,332 B1 | 10/2002 | Mosel et al. |
| 6,461,378 B1 | 10/2002 | Knowlton |
| 6,463,331 B1 | 10/2002 | Edwards |
| 6,470,216 B1 | 10/2002 | Knowlton |
| 6,478,791 B1 | 11/2002 | Carter et al. |
| 6,480,746 B1 | 11/2002 | Ingle et al. |
| 6,482,204 B1 | 11/2002 | Lax et al. |
| 6,494,882 B1 | 12/2002 | Lebouitz et al. |
| 6,533,780 B1 | 3/2003 | Laird et al. |
| 6,546,934 B1 | 4/2003 | Ingle et al. |
| 6,558,381 B2 | 5/2003 | Ingle et al. |
| 6,569,160 B1 | 5/2003 | Goldin et al. |
| 6,572,639 B1 | 6/2003 | Ingle et al. |
| 6,579,266 B2 | 6/2003 | Mosel et al. |
| 6,587,731 B1 | 7/2003 | Ingle et al. |
| 6,607,525 B2 | 8/2003 | Franco |
| 6,629,535 B2 | 10/2003 | Ingle et al. |
| 6,629,974 B2 | 10/2003 | Penny et al. |
| 6,679,875 B2 | 1/2004 | Honda et al. |
| 6,681,771 B2 | 1/2004 | Durette |
| 6,685,623 B2 | 2/2004 | Presthus et al. |
| 6,692,490 B1 | 2/2004 | Edwards |
| 6,743,165 B2 | 6/2004 | Mosel et al. |
| 6,749,624 B2 | 6/2004 | Knowlton |
| 6,751,507 B2 | 6/2004 | Morrison et al. |
| 6,772,013 B1 | 8/2004 | Ingle et al. |
| 6,776,779 B1 | 8/2004 | Roy et al. |
| 6,830,052 B2 | 12/2004 | Carter et al. |
| 6,836,688 B2 | 12/2004 | Ingle et al. |
| 6,840,954 B2 | 1/2005 | Dietz et al. |
| 6,852,110 B2 | 2/2005 | Roy et al. |
| 6,875,209 B2 | 4/2005 | Zvuloni et al. |
| 6,879,858 B1 | 4/2005 | Adams |
| 6,882,885 B2 | 4/2005 | Levy, Jr. et al. |
| 6,889,090 B2 | 5/2005 | Kreindel |
| 6,976,492 B2 | 12/2005 | Ingle et al. |
| 7,004,942 B2 | 2/2006 | Laird et al. |
| 7,022,121 B2 | 4/2006 | Stern et al. |
| 7,104,990 B2 | 9/2006 | Jenkins et al. |
| 7,141,049 B2 | 11/2006 | Stern et al. |
| 7,167,757 B2 | 1/2007 | Ingle et al. |
| 7,238,183 B2 | 7/2007 | Kreindel |
| 7,294,127 B2 | 11/2007 | Leung et al. |
| 7,315,762 B2 | 1/2008 | Mosher et al. |
| 7,473,251 B2 | 1/2009 | Knowlton et al. |
| 7,479,140 B2 | 1/2009 | Ellman et al. |
| 7,536,225 B2 | 5/2009 | Spraker et al. |
| 7,630,774 B2 | 12/2009 | Karni et al. |
| 7,792,589 B2 | 9/2010 | Levy, Jr. et al. |
| 7,837,682 B2 | 11/2010 | Ostrovsky et al. |
| 7,850,683 B2 | 12/2010 | Elkins et al. |
| 7,998,137 B2 | 8/2011 | Elkins et al. |
| 8,121,704 B2 | 2/2012 | Schenck |
| 8,262,715 B2 | 9/2012 | Wong, Jr. et al. |
| 8,285,392 B2 | 10/2012 | Schenck |
| 8,317,782 B1 | 11/2012 | Ellman et al. |
| 8,409,185 B2 | 4/2013 | Burger et al. |
| 8,475,507 B2 | 7/2013 | Dewey et al. |
| 8,515,553 B2 | 8/2013 | Schenck |
| 8,603,084 B2 | 12/2013 | Fish et al. |
| 8,702,691 B2 | 4/2014 | Weber et al. |
| 8,709,057 B2 | 4/2014 | Tettamanti et al. |
| 8,788,060 B2 | 7/2014 | Nebrigic et al. |
| 8,882,758 B2 | 11/2014 | Nebrigic et al. |
| 8,961,511 B2 | 2/2015 | Parmer |
| 9,149,322 B2 | 10/2015 | Knowlton |
| 9,161,802 B2 | 10/2015 | Przybyszewski |
| 9,271,785 B2 | 3/2016 | Parmer et al. |

(56) References Cited

U.S. PATENT DOCUMENTS

| | | |
|---|---|---|
| 2002/0032441 A1 | 3/2002 | Ingle et al. |
| 2002/0049483 A1 | 4/2002 | Knowlton |
| 2002/0062142 A1 | 5/2002 | Knowlton |
| 2002/0120260 A1 | 8/2002 | Morris et al. |
| 2002/0151887 A1 | 10/2002 | Stern et al. |
| 2002/0156471 A1 | 10/2002 | Stern et al. |
| 2002/0183735 A1 | 12/2002 | Edwards et al. |
| 2003/0028180 A1 | 2/2003 | Franco |
| 2003/0097162 A1 | 5/2003 | Kreindel |
| 2003/0120326 A1 | 6/2003 | Dietz et al. |
| 2003/0130575 A1 | 7/2003 | Desai |
| 2003/0139740 A1 | 7/2003 | Kreindel |
| 2003/0139790 A1 | 7/2003 | Ingle et al. |
| 2003/0144576 A1 | 7/2003 | Presthus et al. |
| 2003/0178032 A1 | 9/2003 | Ingle et al. |
| 2003/0195593 A1 | 10/2003 | Ingle et al. |
| 2003/0195604 A1 | 10/2003 | Ingle et al. |
| 2003/0199866 A1 | 10/2003 | Stern et al. |
| 2003/0212393 A1 | 11/2003 | Knowlton et al. |
| 2003/0212395 A1 | 11/2003 | Woloszko et al. |
| 2003/0216728 A1 | 11/2003 | Stern et al. |
| 2003/0216729 A1 | 11/2003 | Marchitto et al. |
| 2003/0220635 A1 | 11/2003 | Knowlton et al. |
| 2003/0236487 A1 | 12/2003 | Knowlton |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0030332 A1 | 2/2004 | Knowlton et al. |
| 2004/0034346 A1 | 2/2004 | Stern et al. |
| 2004/0034400 A1 | 2/2004 | Ingle et al. |
| 2004/0049251 A1 | 3/2004 | Knowlton |
| 2004/0102824 A1 | 5/2004 | Sharkey et al. |
| 2004/0111087 A1 | 6/2004 | Stern et al. |
| 2004/0111136 A1 | 6/2004 | Sharkey et al. |
| 2004/0111137 A1 | 6/2004 | Sharkey et al. |
| 2004/0127895 A1 | 7/2004 | Flock et al. |
| 2004/0162554 A1 | 8/2004 | Lee et al. |
| 2004/0172291 A1 | 9/2004 | Knowlton |
| 2004/0186535 A1 | 9/2004 | Knowlton |
| 2004/0193238 A1 | 9/2004 | Mosher et al. |
| 2004/0206365 A1 | 10/2004 | Knowlton |
| 2004/0210214 A1 | 10/2004 | Knowlton |
| 2004/0210282 A1 | 10/2004 | Flock et al. |
| 2004/0236177 A1 | 11/2004 | Matlock |
| 2004/0236393 A1 | 11/2004 | Ingle et al. |
| 2004/0249425 A1 | 12/2004 | Roy et al. |
| 2004/0260368 A1 | 12/2004 | Ingle et al. |
| 2004/0267336 A1 | 12/2004 | Morrison et al. |
| 2005/0154433 A1 | 7/2005 | Levy et al. |
| 2005/0171582 A1 | 8/2005 | Matlock |
| 2005/0171583 A1 | 8/2005 | Mosher et al. |
| 2005/0187599 A1 | 8/2005 | Sharkey et al. |
| 2005/0203399 A1 | 9/2005 | Vaezy et al. |
| 2005/0288544 A9 | 12/2005 | Matlock |
| 2005/0288680 A1 | 12/2005 | Ingle et al. |
| 2006/0025837 A1 | 2/2006 | Stern et al. |
| 2006/0047331 A1 | 3/2006 | Lax et al. |
| 2006/0167533 A1 | 7/2006 | Spraker et al. |
| 2006/0224090 A1 | 10/2006 | Ostrovsky et al. |
| 2006/0241530 A1 | 10/2006 | Ostrovsky et al. |
| 2007/0078502 A1 | 4/2007 | Weber et al. |
| 2007/0083247 A1 | 4/2007 | Wyeth et al. |
| 2007/0088413 A1 | 4/2007 | Weber et al. |
| 2007/0093807 A1 | 4/2007 | Baxter et al. |
| 2007/0106349 A1 | 5/2007 | Karni et al. |
| 2007/0219602 A1 | 9/2007 | Ostrovsky et al. |
| 2007/0233191 A1 | 10/2007 | Parmer |
| 2008/0200969 A1 | 8/2008 | Weber |
| 2009/0163807 A1 | 6/2009 | Sliwa |
| 2010/0049186 A1 | 2/2010 | Ingle et al. |
| 2011/0004205 A1 | 1/2011 | Chu et al. |
| 2011/0178584 A1 | 7/2011 | Parmer et al. |
| 2012/0016239 A1 | 1/2012 | Barthe et al. |
| 2012/0046547 A1 | 2/2012 | Barthe et al. |
| 2012/0089211 A1 | 4/2012 | Curtis et al. |
| 2012/0136407 A1 | 5/2012 | Presthus et al. |
| 2012/0239122 A1 | 9/2012 | Dong et al. |
| 2012/0259322 A1 | 10/2012 | Fourkas et al. |
| 2013/0060309 A1 | 3/2013 | Bradley |
| 2013/0096431 A1 | 4/2013 | Vaezy et al. |
| 2013/0200549 A1 | 8/2013 | Felts et al. |
| 2013/0237979 A1 | 9/2013 | Shikhman et al. |
| 2013/0245728 A1 | 9/2013 | Galen et al. |
| 2014/0148878 A1 | 5/2014 | Khatri |
| 2014/0257145 A1 | 9/2014 | Emery |
| 2014/0303697 A1 | 10/2014 | Anderson et al. |
| 2014/0324036 A1 | 10/2014 | Sachs et al. |
| 2015/0165241 A1 | 6/2015 | Burdette |
| 2015/0202467 A1 | 7/2015 | Diederich et al. |
| 2015/0216720 A1 | 8/2015 | DeBenedictis et al. |
| 2015/0297908 A1 | 10/2015 | Alinsod et al. |
| 2015/0327926 A1 | 11/2015 | Parmer |
| 2016/0095643 A1 | 4/2016 | Fourkas et al. |
| 2016/0135876 A1 | 5/2016 | Parmer et al. |
| 2016/0183996 A1 | 6/2016 | Burger et al. |
| 2016/0183998 A1 | 6/2016 | Fourkas et al. |
| 2016/0296278 A1 | 10/2016 | Galen et al. |
| 2017/0028213 A1 | 2/2017 | Courtion et al. |
| 2017/0028227 A1 | 2/2017 | Emery et al. |

FOREIGN PATENT DOCUMENTS

| | | |
|---|---|---|
| CN | 2454769 Y | 10/2001 |
| CN | 1778414 A | 5/2006 |
| CN | 1868396 A | 11/2006 |
| CN | 2885157 Y | 4/2007 |
| CN | 2897183 Y | 5/2007 |
| CN | 101229078 A | 7/2008 |
| CN | 101273874 A | 10/2008 |
| CN | 201286935 Y | 8/2009 |
| CN | 101810505 A | 8/2010 |
| CN | 202724094 U | 2/2013 |
| CN | 202751492 U | 2/2013 |
| CN | 202859437 U | 4/2013 |
| CN | 103300961 A | 9/2013 |
| EP | 0253677 B1 | 9/1993 |
| JP | H05269144 A | 10/1993 |
| JP | H09122141 A | 5/1997 |
| JP | H09-140802 A | 6/1997 |
| JP | H11504828 A | 5/1999 |
| JP | 2000507118 A | 6/2000 |
| JP | 2001514921 A | 9/2001 |
| JP | 2002238919 A | 8/2002 |
| JP | 2003503118 A | 1/2003 |
| JP | 2005198896 A | 7/2005 |
| JP | 2005318953 A | 11/2005 |
| JP | 2006-517422 A | 7/2006 |
| JP | 2006187668 A | 7/2006 |
| KR | 20100087521 A | 8/2010 |
| KR | 20120010737 A | 2/2012 |
| RU | 2125846 C1 | 2/1999 |
| RU | 2207823 C2 | 7/2003 |
| RU | 2217186 C1 | 11/2003 |
| RU | 2291673 C1 | 1/2007 |
| TW | 200305649 A | 11/2003 |
| TW | 200724083 A | 7/2007 |
| TW | 200831152 A | 8/2008 |
| TW | 200938247 A | 9/2009 |
| WO | 94/26345 A1 | 11/1994 |
| WO | 95/10981 A1 | 4/1995 |
| WO | 96/22739 A1 | 8/1996 |
| WO | 96034568 A1 | 11/1996 |
| WO | 97029701 A1 | 8/1997 |
| WO | 97/34534 A1 | 9/1997 |
| WO | 98/019613 A1 | 5/1998 |
| WO | 99/08614 A1 | 2/1999 |
| WO | 99/53853 A1 | 10/1999 |
| WO | 2000/010475 A1 | 3/2000 |
| WO | 2001000269 A1 | 1/2001 |
| WO | 01/80723 A2 | 11/2001 |
| WO | 02/07657 A1 | 1/2002 |
| WO | 2003011158 A1 | 2/2003 |
| WO | 2003053355 A2 | 7/2003 |
| WO | 2005/063138 A1 | 7/2005 |

(56) References Cited

FOREIGN PATENT DOCUMENTS

| WO | 2006/033067 A2 | 3/2006 |
|---|---|---|
| WO | 2006/034357 A2 | 3/2006 |
| WO | 2006/103678 A2 | 10/2006 |
| WO | 2006/105121 A2 | 10/2006 |
| WO | 2008/153999 A1 | 12/2008 |
| WO | 2011034986 A2 | 3/2011 |
| WO | 2011/066445 A2 | 6/2011 |
| WO | 2014165242 A1 | 10/2014 |
| WO | 2016004295 A1 | 1/2016 |

OTHER PUBLICATIONS

Bergman et al., "Role of the Q-tip Test in Evaluating Stress Urinary Incontinence" The Journal of reproductive medicine, 32(4):273-5 (1987).
Weigel et al., "The Female Sexual Function Index (FSFI): Cross-Validation and Development of Clinical Cutoff Scores" Journal of Sex & Marital Therapy, 31:1-20 (2005).
Verrico et al., "Expression of the collagen-related heat shock protein HSP47 in fibroblasts treated with hyperthermia or photodynamic therapy" British Journal of Cancer (76(6):719-724 (1997).
Uebersax et al., "Short Forms to Assess Life Quality and Symptom Distress for Urinary Incontinence in Women: The Incontinence Impact Questionnaire and the Urogenital Distress Inventory" Neurourology and Urodynamics 14: 131-139 (1995).
Harvey et al., "The Incontinence Impact Questionnaire and the Urogenital Distress Inventory: A revisit of their validity in women without a urodynamic diagnosis" Am J Obstet Gynecol, 185:25-31 (2001).
Tähtinen et al., "Long-term Impact of Mode of Delivery on Stress Urinary Incontinence and Urgency Urinary Incontinence: A Systematic Review and Meta-analysis" European Urology 70:148-158 (2016).
Shumaker et al., "Health-Related Quality of Life Measures for Women with Urinary Incontinence: the Incontinence Impact Questionnaire and the Urogenital Distress Inventory" Quality of Life Research, 3, pp. 291-306 (1994).
Sekiguchi et al., "Laxity of the Vaginal Introitus After Childbirth: Nonsurgical Outpatient Procedure for Vaginal Tissue Restoration and Improved Sexual Satisfaction Using Low-Energy Radiofrequency Thermal Therapy" Journal of Women's Health, 22(9):775-781 (2013).
Sajjadi et al., "Expression of heat shock proteins 70 and 47 in tissues following short-pulse laser irradiation: Assessment of thermal damage and healing" Medical Engineering & Physics, 35(10):1-9 (Apr. 2013).
Rosen et al., "The Female Sexual Function Index (FSFI): A Multidimensional Self-Report Instrument for the Assessment of Female Sexual Function" Journal of Sex & Marital Therapy, 26:191-208 (2000).
Patrick et al., "Quality of Life of Women With Urinary Incontinence: Further Development of the Incontinence Quality of Life Instrument (I-QOL)" Urology 53: 71-76 (1999).
Millheiser et al., "Radiofrequency Treatment of Vaginal Laxity after Vaginal Delivery: Nonsurgical Vaginal Tightening" J Sex Med, 7:3088-3095 (2010).
Krychman et al., "Effect of Single-Treatment, Surface-Cooled Radiofrequency Therapy on Vaginal Laxity and Female Sexual Function: The Viveve I Randomized Controlled Trial" J Sex Med, 14:215-225 (2017).
Krychman et al., "Effect of Single-Session, Cryogen-Cooled Monopolar Radiofrequency Therapy on Sexual Function in Women with Vaginal Laxity: The Viveve I Trial" Journal of Women's Health, 27(3):297-304 (2018).
Krhut et al., "ICS Teaching Module: Pad Weight Testing in the Evaluation of Urinary Incontinence" International Continence Society (Unknown).
Kawasaki et al., "Deletion of the Collagen-specific Molecular Chaperone Hsp47 Causes Endoplasmic Reticulum Stress-mediated Apoptosis of Hepatic Stellate Cells*" The Journal of Biological Chemistry, 290 (6):3639-3646 (2015).
Urinary Incontinence in Women, Practice Bulletin, Clinical Management Guidelines for Obstetrician-Gynecologists, Obstetrics and Gynecology, 126(5):e66-e81 (2015).
Avery et al., "ICIQ: A Brief and Robust Measure for Evaluating the Symptoms and Impact of Urinary Incontinence" Neurourology and Urodynamics 23:322-330 (2004).
Liberate (International) VI-17-01 Evaluation of the Safety and Efficacy of the Viveve Geneveve Treatment for Stress Urinary Incontinence, Clinical Protocol, pp. 1-49 (Apr. 9, 2018).
Macrene, Alexiades, MD, Ph.D., et al. "Randomized, Blinded, 3-Arm Clinical Trial Assessing Optimal Temperature and Duration for Treatment With Minimally Invasive Fractional Radiofrequency", American Society for Dermatologic Surgery, 2015, 41:623-632 (10 pages).
Dany Berube, Ph.D., et al., "A Predictive Model of Minimally Invasive Bipolar Fractional Radiofrequency Skin Treatment", Lasers in Surgery and Medicine, 2009, 41:473-478 (6 pages).
Femilift / Alma Surgical "Clinical Solutions for a Better Feminine Life", retrieved Sep. 16, 2015 from http://www.almasurgical.com/applications/femililift/ (8 pages).
IncontiLase/Gynecology/Fotona, retrieved Sep. 16, 2015 from http://www.fotona.com/en/treatments/1309/incontilase/ (3 pages).
Venn Healthcare Petite Lady, retrieved Sep. 19, 2015 from http://venthealthcare.com/petite-lady (4 pages).
Chinese Office Action, dated Feb. 26, 2019, for Chinese Appl No. 201610244844, filed Mar. 16, 2012 w/English Translation.
Taiwanese Office Action, dated Apr. 10, 2019, for Taiwanese Appl No. 106103270, filed Mar. 14, 2013.
Indian Office Action, dated Oct. 26, 2018, for Indian Appl No. 2321/DELNP/2012, filed Sep. 16, 2010 w/English Translation.
U.S. Office Action, dated Jul. 18, 2019, for U.S. Appl. No. 14/629,186, filed Feb. 23, 2015.
Chinese Office Action, dated Feb. 11, 2019, for Chinese Appl No. 201610223768.4, filed Apr. 12, 2016 w/English Translation.
U.S. Office Action, dated Jun. 27, 2019, for U.S. Appl. No. 15/268,398, filed Sep. 16, 2016.
Japanese Office Action, dated Feb. 27, 2019, for Japanese Appl No. 2017-3686, filed Mar. 15, 2013 w/English Translation.
U.S. Office Action, dated May 28, 2019, for U.S. Appl. No. 15/188,948, filed Jun. 21, 2019.
European Office Action, dated Sep. 12, 2018, for European Appl No. 18168440.8, filed Mar. 15, 2013.
Korean Office Action, dated Oct. 19, 2018, for Korean Appl No. 10-2017-7015034, filed Mar. 15, 2013.
Alinsod Institute for Aesthetic Vaginal Surgery; About Dr. Red Alinsod; 1 pg.; retrieved Feb. 21, 2017 from the internet at: http:/www.vaginalrejuvenationtraining.org/about.shtml.
Alinsod; What are the differences between thermiva radiofrequency and femlift/monalisa/intimalase lasers for use in aesthetic vulvovaginal therapies; 12 pages: retrieved from the Internet at (https://www.linkedin.com/pulse/what-differences-between-thermiva-radiofrequency-use-alinsod-m-d-/?published=u) on Jan. 16, 2017.
Beattie et al.; UVA1 phototherapy for genital lichen sclerosus; Clinical and Experimental Dermatology; 31(3); pp. 343-347; May 1, 2006.
Bieber et al. (Ed.); The Gynecologic resectoscope; Chapter # the tissue effects of radiofrequency electrosurgical currents; Blackwell Science, Inc.; pp. 27-46; (year of pub. sufficiently earlier than effective US filing date and any foreign priority date); 1995.
Dmochowski et al., Transvaginal Radio Frequency Treatment of the Endopelvic Fascia: A Prospective Evaluation for the Treatment of Genuine Stress Urinary Incontinence, 169(3), J. Or Urology, pp. 1028-1032, Mar. 2003.
Dmochowski, Radiofrequency Bladder Neck Suspension for the Treatment of Genuine Stress Urinary Incontinence, Current Urology Reports, 3(5), pp. 378-381, Oct. 2002.
Kreuter et al.; Low-dose ultraviolet Al phototherapy for extragenital lichen sclerosus: results of preliminary study; Journal of the American Academy of Dermatology; 46(2); pp. 251-255; Feb. 2002.
Laser Vaginal Rejuvenation Center of Los Angeles, Laser Vaginal Rejuvenation for the Enhancement of Sexual Gratification: About

(56) References Cited

OTHER PUBLICATIONS

Dr. Matlock, 8 pgs., © 2000, retrieved Mar. 30, 2017 at: https://web.archive.org/web/20001002113647/http:/www.drmatlock.com/laserVR.htm.
Lenihan, Jr., Comparison of the Quality of Life After Nonsurgical Radiofrequency Energy Tissue Micro-Remodeling in Premenopausal and Postmenopausal Women With Moderate-to-Severe Stress Urinary Incontinence, Am. J. Of Obstetrics and Gynecology, 192(6), pp. 1995-2001, Jun. 2005.
Ollivier, Designer Vaginas, Salon, 4 pgs., Nov. 14, 2000, retrieved Mar. 30, 2017 at http://www.salon.com/2000/11/14/vagina_3/.
Peterson et al.; Successful carbon dioxide laser therapy for refractory anogenital lichen sclerosus; Dermatologic Surgery; 30(8); pp. 1148-1151; Aug. 1, 2004.
Reid et al., Flashlamp-Excited Dye Laser Therapy of Idiopathic Vulvodynia is Safe and Efficacious, Am. J. Obstet. Gynecol., 172(6), pp. 1684-1701, Jun. 1995.
Ross et al., A Prospective Multisite Study of Radiofrequency Bipolar Energy for Treatment of Genuine Stress Incontinence, J. Of the American Association of Gynecologic Laparoscopists, 9 (4), pp. 493-499, Nov. 2002.
Smith et al.; Vulvar lichen sclerosus; American Journal of Clinical Dermatology; 5(2); pp. 105-125; (Author Manuscript) Apr. 1, 2004.
Sotomayor et al., Twelve-Month Results of Nonsurgical Radiofrequency Energy Micro-Remodeling for Stress Incontinence, 16 Int. Urogynecol. J., 16(3), pp. 192-196, May-Jun. 2004.
Taber's Cyclopedic Medical Dictionary: Ablation (definition); F. A. Davies Company; 3 pages; (year of pub. sufficiently earlier than effective US filing date and any foreign priority date) 2005.
Thermigen, LLC; Ask Your Doctor How Controlled Radiofrequency Might Benefit You, THERMIva (advertisement); document No. MA-PA-TVA2 Rev A; 1 page; this web address was available to applicant(s) at least as of Feb. 23, 2017.
Thermigen, LLC; Everyone Is Talking About the Benefits of Temperature Controlled Radiofrequency, THERMIva (advertisement); document No. MC-TVA-03 Rev B; 2 pgs.; this web address was available to applicant(s) at least as of Feb. 23, 2017.
Thermigen, LLC; Now Offering...THERMIva (physician advertisement); document No. MA-PA-TVA1 Rev A; 1 page; this web address was available to applicant(s) at least as of Feb. 23, 2017.
Thermigen, LLC; The Science of Heat, The Beauty of Control. THERMIva (product information); document No. MA-PY-TVA-1 Rev A; 1 page; this web address was available to applicant(s) at least as of Feb. 23, 2017.
Thermigen, LLC; THERMIva Non-Surgical Vulvovaginal Rejuvination (product advertisement); 1 page; this web address was available to applicant(s) at least as of Feb. 23, 2017.
Thermigen, LLC; THERMIva: Minimally-Invasive Electrocoagulation (product information); document No. MC-TVA 04 Rev B; 1 pg.; this web address was available to applicant(s) at least as of Feb. 23, 2017.
ThermiVa: Doctors are Weighing in on ThermiVa; 4 pages; retrieved from the internet (http://thermiva.org/doctors-are-wieghing-in.) on Aug. 20, 2015.
Webster's Third New International Dictionary; Over (definition); Merriam-Webster, Inc.; 3 pages; (year of pub. sufficiently earlier than effective US filing date and any foreign priority date) 2002.
Zelickson et al., Histological and Ultrastructural Evaluation of the Effects of a Radiofrequency-Based Nonablative Dermal Remodeling Device: A Pilot Study, Arch Dermatol, 140(2), pp. 204-209, Feb. 2004.
PCT International Search Report, dated May 9, 2011, for Intentional App'l No. PCT/US2010/049045, filed Sep. 16, 2010.
PCT Written Opinion of the International Searching Authority, dated May 9, 2011, for Intentional App'l No. PCT/US2010/049045, filed Sep. 16, 2010.
Chinese Search Report, dated Apr. 12, 2013, for Chinese App'l No. 201220099603,8, filed Mar. 16, 2012 (with English translation).
Chinese Search Report, dated Apr. 12, 2013, for Chinese App'l No. 201220099605.7, filed Mar. 16, 2012 (with English translation).
Chinese Search Report, dated Apr. 12, 2013, for Chinese App'l No. 201220099618.4, filed Mar. 16, 2012 (with English translation).
Chinese Search Report, dated Apr. 12, 2013, for Chinese App'l No. 201220099620.1, filed Mar. 16, 2012 (with English translation).
Chinese Search Report, dated Apr. 12, 2013, for Chinese App'l No. 201220099634.3, filed Mar. 16, 2012 (with English translation).
Chinese Search Report, dated Apr. 12, 2013, for Chinese App'l No. 201220099648.5, filed Mar. 16, 2012 (with English translation).
PCT International Search Report, dated Jun. 6, 2013, for Intentional App'l No. PCT/US2013/032066, filed Mar. 15, 2013.
PCT Written Opinion of the International Searching Authority, dated Jun. 6, 2013, for Intentional App'l No. PCT/U52013/032066, filed Mar. 15, 2013.
U.S. Office Action, dated Oct. 9, 2013, for U.S. Appl. No. 12/884,108, filed Sep. 16, 2010.
U.S. Office Action, dated Feb. 6, 2014, for U.S. Appl. No. 12/884,108, filed Sep. 16, 2010.
Chinese Office Action, dated Aug. 26, 2014, for Chinese App'l No. 201210069909.3, filed Mar. 16, 2012.
U.S. Office Action, dated Aug. 27, 2014, for U.S. Appl. No. 12/884,108, filed Sep. 16, 2010.
Chinese Office Action, dated Sep. 4, 2014, for Chinese Appl1 No. 201210069910.6, filed Mar. 16, 2012.
Chinese Office Action, dated Sep. 4, 2014, for Chinese Appl1 No. 201210069906,X, filed Mar. 16, 2012.
U.S. Office Action, dated Mar. 17, 2015, for U.S. Appl. No. 12/884,108, filed Sep. 16, 2010.
Extended European Search Report, dated Mar. 24, 2015, for European App'l No. EP13760612.5, filed Mar. 15, 2013.
Chinese Office Action, dated Mar. 24, 2015, for Chinese App'l No. 201210069906.X, filed Mar. 16, 2012.
Russian Office Action, dated Jan. 10, 2017, for Russian App'l No. RU 2014141309, filed Oct. 16, 2014.
Jun. 8, 2018 Office Action for CN201610223768,4.
Dec. 12, 2017 Office Action for CN201610244844.X.
May 1, 2017 Notice of Dismissal of Amendment for KR10-2014-7029000.
Oct. 19, 2018 Office Action for KR10-2017-7015034.
Aug. 27, 2018 Office Action for JP2017-003686.

METHODS FOR TREATING URINARY STRESS INCONTINENCE

CROSS-REFERENCE TO RELATED APPLICATION

This application claims priority to U.S. Provisional Patent Application No. 62/690,534, filed on Jun. 27, 2018; the entire contents of which are hereby incorporated by reference.

FIELD OF THE INVENTION

Aspects of the invention relate to methods for treating urinary stress incontinence via the non-invasive application of energy to vaginal tissue to induce tissue remodeling.

BACKGROUND

The vagina is made up of four layers, 1) a mucosa of stratified squamous epithelial tissue; 2) the submucosa or lamina propria containing vascularized connective tissue; 3) a deeper muscularis, containing smooth muscle; and 4) an adventitia comprising a thick layer of connective tissue. The uppermost layers of epithelial cells are often referred to as the mucosal epithelium. Collagen molecules are produced by cells resident in these tissues that synthesize three polypeptide chains that wrap around one another to form a triple helix. Collagen is a type of protein that is a basic structural element of connective tissue, tendons, cartilage, and bone. Each collagen chain is approximately 1000 amino acid units in length, with glycine recurring regularly every third unit, and with proline and hydroxyproline recurring very frequently. Cross-linking occurs between the sides, not the ends, of collagen molecules, and is coupled with the amino acid composition to give collagen its great strength.

Vaginal tissue can undergo change for a variety of reasons. For example, vaginal tissue is stretched during vaginal child birth; at least some of the effects of the stretching are permanent, and many women have long-term medical, social and quality of life consequences. Some consequences include physical problems, such as urinary stress incontinence, for which surgical intervention may be required.

Urinary incontinence is a socially disabling condition that affects millions of women of all ages and ethnicities. Urinary stress incontinence is defined by the involuntary loss of urine during increased intra-abdominal pressure in the absence of a detrusor contraction. Increased intra-abdominal pressure can be caused by coughing, sneezing, laughing, exercising, and lifting heavy objects, for example. Urinary stress incontinence is the most common type of female urinary incontinence, affecting more than an estimated 7 million women in the United States. Current methods of treatment of urinary stress incontinence are typically invasive. Accordingly, there is a need for a non-invasive, non-pharmaceutical treatment for urinary stress incontinence in women.

SUMMARY OF THE INVENTION

An embodiment of the invention relates to a method for treating urinary stress incontinence in a subject, the method including: non-invasively delivering energy to one or more submucosal regions of a vaginal tissue, thereby heating the one or more submucosal regions to a predetermined temperature; and remodeling the one or more submucosal regions of the vaginal tissue of the subject to treat the subject for urinary stress incontinence. In such an embodiment, the one or more submucosal regions are located within 4 predetermined quadrants around a vaginal canal, the one or more submucosal regions comprise 20 target tissue locations, such that each of the 4 predetermined quadrants comprises 5 target tissue locations, non-invasively delivering energy comprises executing at least 10 energy delivery passes in each of the 4 predetermined quadrants, each of the energy delivery passes comprises applying in a predetermined order 1 to 5 energy pulses to each of the 5 target tissue locations in each of the 4 predetermined quadrants, and non-invasively delivering energy comprises delivering at least 20 energy pulses to two or more submucosal regions of a vaginal tissue that is located alongside a urethra of the subject.

An embodiment of the invention relates to the method above, where the executing at least 10 energy delivery passes in each of the 4 predetermined quadrants comprises: executing a first series of 5 energy delivery passes in each of the 4 predetermined quadrants; and executing a second series of 5 energy delivery passes in each of the 4 predetermined quadrants. In such an embodiment, the first series of 5 energy delivery passes in each quadrant is completed before the second series of 5 energy delivery passes in each of the 4 predetermined quadrants is initiated, and each of the first series of 5 energy delivery passes and the second series of 5 energy delivery passes comprises applying in a predetermined order 1 energy pulse to each of the 5 target tissue locations in each of the 4 predetermined quadrants.

An embodiment of the invention relates to the method above, where the delivering up to 20 energy pulses to two or more submucosal regions located alongside the urethra comprises: delivering a first series of 10 energy pulses to the two or more submucosal regions located alongside the urethra; and delivering a second series of 10 energy pulses to the two or more submucosal regions located alongside the urethra. In such an embodiment, the first series of 10 or more pulses is delivered after the executing the first series of up to 5 energy delivery passes in each of the 4 predetermined quadrants, and the second series of 10 or more pulses is delivered after the executing the second series of up to 5 energy delivery passes in each of the 4 predetermined quadrants.

An embodiment of the invention relates to the method above, where executing each energy delivery pass of the first series of 5 energy delivery passes in each of the 4 predetermined quadrants comprises applying in a predetermined order 1 energy pulse to each of a first set of 5 target tissue locations in each of the 4 predetermined quadrants such that each target tissue location of the first set of 5 target tissue locations at least partially overlaps with an adjacent target tissue location. In such an embodiment, executing each energy delivery pass of the second series of 5 energy delivery passes in each of the 4 predetermined quadrants comprises applying in a predetermined order 1 energy pulse to each of a second set of 5 target tissue locations in each of the 4 predetermined quadrants, such that each target tissue location of the second set of 5 target tissue locations at least partially overlaps with an adjacent target tissue location.

An embodiment of the invention relates to the method above, where each target tissue location of the second set of 5 target tissue locations in each of the 4 predetermined quadrants is proximal to each target tissue location of the first set of 5 target tissue locations in each of the 4 predetermined quadrants. In such an embodiment, the first set of 5 target tissue locations in each of the 4 predetermined quadrants are located proximal to the introitus, while the second set of 5 target tissue locations in each of the 4 predetermined quadrants are located further into the vaginal canal and proximate to the first set of 5 target tissue locations. In some embodiments, each target tissue location of the second set of 5 target tissue locations in each of the 4 predetermined quadrants at least partially overlaps with at least one target tissue location of the first set of 5 target tissue locations in each of the 4 predetermined quadrants. In alternative embodiments, the first set of 5 target tissue locations in each of the 4 predetermined quadrants and the second set of 5 target tissue locations in each of the 4 predetermined quadrants do not overlap.

An embodiment of the invention relates to the method above, where the first series of 10 energy pulses and the second series of 10 energy pulses are delivered to two submucosal regions, a first submucosal region of the two submucosal regions is located within a target tissue located on a first side of the urethra, a second submucosal region of the two submucosal regions is located within a target tissue located on a second side of the urethra, and each energy pulse of the first set of 10 energy pulses and the second set of 10 energy pulses is applied in an alternating manner to the first submucosal region and to the second submucosal region such that two or more energy pulses are not applied in a consecutive manner to a same submucosal region.

An embodiment of the invention relates to the method above, where executing the first series of 5 energy delivery passes in each of the 4 predetermined quadrants comprises: executing 5 energy delivery passes in a first quadrant; executing 5 energy delivery passes in a second quadrant after the executing 5 energy delivery passes in the first quadrant; executing 5 energy delivery passes in a third quadrant after the executing 5 energy delivery passes in the second quadrant; and executing 5 energy delivery passes in a fourth quadrant after the executing 5 energy delivery passes in the third quadrant.

An embodiment of the invention relates to the method above, where remodeling the one or more submucosal regions comprises changing a structural organization and/or biomechanical property of an existing collagen molecule, strengthening or bolstering a collagen-rich site in the one or more submucosal regions, releasing one or more heat shock proteins or other cellular cascades in the one or more submucosal regions, stimulating cellular production and/or deposition of collagen into an extracellular space, or any combination thereof.

An embodiment of the invention relates to the method above, where the 4 predetermined quadrants comprise a first quadrant from a 12 o'clock position to a 3 o'clock position, a second quadrant from the 3 o'clock position to a 6 o'clock position, a third quadrant is from the 6 o'clock position to a 9 o'clock position, and a fourth quadrant is from the 9 o'clock position to the 12 o'clock position, and wherein the urethra of the subject is located at the 12 o'clock position.

An embodiment of the invention relates to the method above, where the predetermined temperature is between 38° C. to 46° C.

An embodiment of the invention relates to the method above, where the predetermined temperature is between 40° to 46° C.

An embodiment of the invention relates to the method above, where the predetermined temperature is between 40° to 42° C.

An embodiment of the invention relates to the method above, where non-invasively delivering energy comprises applying radiofrequency energy.

An embodiment of the invention relates to the method above, where non-invasively delivering energy comprises applying microwave energy.

An embodiment of the invention relates to the method above, where non-invasively delivering energy comprises applying ultrasound energy.

An embodiment of the invention relates to the method above, where the energy delivery is controlled by a feedback control mechanism, such that the predetermined temperature is not exceeded.

An embodiment of the invention relates to the method above, where the feedback control is provided by one or more thermal sensors.

An embodiment of the invention relates to the method above, where the feedback control is provided by one or more impedance monitors.

An embodiment of the invention relates to the method above, further including cooling an epithelial tissue layer above the one or more submucosal regions.

An embodiment of the invention relates to the method above, where the epithelial tissue layer is cooled to a temperature that ranges from 0° to 10° C.

An embodiment of the invention relates to the method above, where the cooling precedes the heating, and continues during the energy delivery.

An embodiment of the invention relates to the method above, where the cooling is during the heating, and continues after the energy delivery.

An embodiment of the invention relates to the method above, where the combination of cooling and non-invasively delivering energy creates a reverse thermal gradient from a surface layer to the one or more submucosal regions.

An embodiment of the invention relates to the method above, where the energy delivery does not substantially modify a mucosal epithelium of the vaginal tissue.

An embodiment of the invention relates to the method above, further including altering a conformation of the vaginal tissue.

An embodiment of the invention relates to the method above, where at least some of the remodeling occurs during the non-invasive energy delivery.

An embodiment of the invention relates to the method above, where at least some of the remodeling occurs after the non-invasive energy delivery.

INCORPORATION BY REFERENCE

U.S. Patent Publication No. 2017/0071651, filed on Sep. 16, 2016 is incorporated by reference. All publications and patent applications identified herein are incorporated by reference in their entirety and to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

DETAILED DESCRIPTION OF THE INVENTIONS

Figure 1:
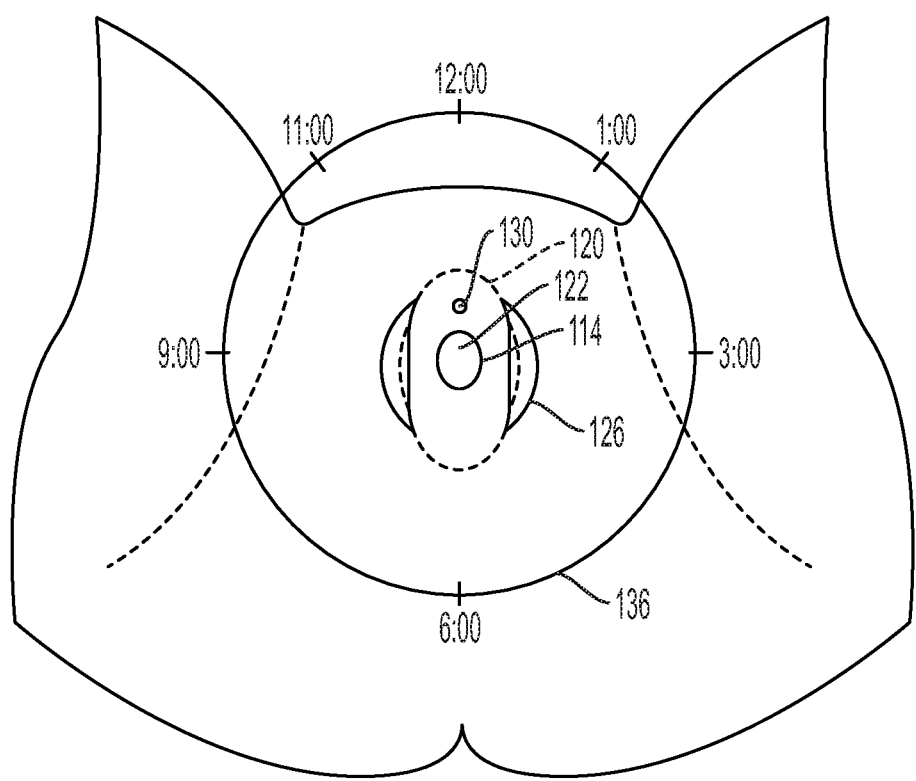
FIG. 1 is a schematic view of female genitalia depicting the mucosal epithelial surfaces that overlay the target tissue, as well as an orienting clock to provide a circumferential reference scheme for the vagina wall.

In some embodiments, a target tissue lies immediately beneath a mucosal epithelium of a genital tissue, and includes the lamina propria, a connective tissue that includes the majority collagen in the extracellular space, adjacent to the muscularis, which includes smooth muscle. In some embodiments, a therapeutic zone of tissue includes one or more of the first two layers of the vagina, which are the mucosa of stratified squamous epithelial tissue and the submucosa or lamina propria containing vascularized connective tissue. In some embodiments, a therapeutic zone of tissue includes only the second layer of the vagina, which is the submucosa or lamina propria containing vascularized connective tissue. A therapeutic zone of tissue in accordance with embodiments of the invention does not include direct treatment of deeper tissue, such as endopelvic fascia, although application of the subject methods may alleviate strain on these and other tissues.

Aspects of the invention include methods for non-invasive treatment of lower portions of the vagina. The lower portions of the vagina are the portions immediately inward from the introitus. One embodiment of the invention provides a non-surgical and non-invasive method for inducing tissue remodeling by applying energy to an area inside the vagina. In particular, the target area is inside the vagina directly proximal to the hymenal ring, and the application of energy to a target tissue induces remodeling of the targeted tissue. Thus, according to an embodiment of the invention, the portion of the vagina to be treated is a region between the hymen and a position located no further than about 4 to 6 cm inward from the hymen, depending on the condition being treated.

Aspects of the invention include methods for treating the connective tissue underlying the mucosal epithelium, wherein the methods do not damage the epithelium itself. In some embodiments, cooling of the epithelium is used as protective measure. Methods in accordance with embodiments of the invention are non-invasive and non-ablative of genital tissue.

The anatomical areas of the female genitalia treated via the methods described herein include the vulva and the vagina (including the introitus, the opening of the vagina). The vulva includes tissue radiating outward from the introitus to Hart's line, where mucosal epithelium gives way to skin on the outer surface of the labia minora. With more specific regard to the vagina, aspects of the invention include methods of treating the lower portion of the vagina, a portion extending from the introitus to a location from about 2 cm to about 4 cm inward from the introitus, in other embodiments the location may extend inward as far as about 6 cm from the hymenal ring. With regard to the circumference of the inner wall of the vagina, a clock position reference scheme is helpful. The urethra is proximal to the anterior wall of the vagina, the location of the vaginal wall nearest the urethra and urethral opening may be considered 12 o'clock. With this reference point, target tissue in accordance with some embodiments of the methods includes an approximately 330 degree arc between 12:30 o'clock and 11:30 o'clock. In some embodiments, the subject methods involve treating an area within the approximately 30 degree arc between 11:30 o'clock and 12:30 o'clock, in the vicinity of the urethra (or alongside the urethra), but specifically avoid the area directly underneath the urethra at 12 o'clock. In some embodiments, the subject methods involve treating the entire 360 degrees of the clock position reference scheme, including the approximately 30 degree arc between 11:30 o'clock and 12:30 o'clock where the urethra is located.

In some embodiments, the methods include applying energy to a target tissue, typically radiofrequency (RF) energy, but other embodiments may use microwave or ultrasound energy. The methods include contacting the mucosal epithelium with a treatment tip that has an energy delivering element and a cooling mechanism. By delivering energy to the tissue while cooling the epithelial surface, a reverse thermal gradient is created. The RF energy penetrates through the cooled epithelium and into the underlying target tissue, resulting in heating of the tissue.

In some embodiments, the tissue that receives the energy and is heated to a threshold temperature (e.g., to a therapeutic temperature that causes remodeling) is considered to be within a therapeutic zone, and is referred to as the therapeutic zone of tissue. In some embodiments, not all tissue within the therapeutic zone necessarily reaches a threshold temperature (or therapeutic level) of heat as a result of the energy application in accordance with the subject methods.

In some embodiments, a mucosal surface or mucosal layer of tissue is cooled during, before and/or concurrently with the application of energy. In such embodiments, the cooling can have an effect on the therapeutic zone, e.g., by moving it deeper within the target tissue, for example, or by altering or constraining its volume.

In some embodiments, energy applied to the target tissue heats the target tissue to a temperature as high as about 46° C. In some embodiments, therapeutic temperature may range between about 38° and 46° C. In other embodiments, the therapeutic temperature may range between about 40° and 46° C. In other embodiments, the therapeutic temperature may range between about 40° and 42° C. Energy delivery is a process subject to feedback control during a treatment procedure, so as to keep the temperature within a predetermined temperature range. Feedback may be provided by one or more thermisters (thermal sensors) or impedance monitors on an apparatus sued for delivering the energy. In some embodiments, a treatment tip on an apparatus cools the epithelium to a temperature between about 0 and 10° C. A reverse thermal gradient, accordingly may be represented by a low temperature of between about 0° and 10° C. at the mucosal epithelium, and between a temperature of between about 38° and 46° C., between about 40° and 46° C., or between about 40° and 42° C. in the therapeutic zone.

In some embodiments, during a typical procedure any period of energy delivery is accompanied by cooling; however cooling may also precede energy delivery, and/or follow energy delivery.

In some embodiments, methods of treatment comprise contacting a contact site on the mucosal epithelium with a probe from an apparatus. In such embodiments, the contact site conforms to the dimensions of a treating surface of a treatment tip on the apparatus. In such embodiments, the apparatus generally includes a treatment probe coupled to a controller. Exemplary systems are disclosed in U.S. Pat.

Nos. 9,271,785 and 8,961,511 and U.S. Patent Publication No. 2017/0071651A1, each of which are incorporated herein by reference in their entirety.

During the course of a single treatment (e.g., what would occur on a visit to a medical office), typically a plurality of contact sites are treated. During a procedure, a single contact site may receive energy delivery multiple times. The summed total of mucosal contact sites comprises a treatment area. Such an area, comprising multiple contact sites, may be recorded on a suitable coordinate system, such as a clock face coordinate system as described herein. The method may be applied on more than one occasion; a patient may return to her physician at a later date when the effects of a previous treatment may be evaluated and a treatment repeated. The treatment areas of the separate procedures may be the same, different, or overlap.

Remodeling of vaginal tissue, per embodiments of the invention, may include changes to collagen molecules that are present within collagen-rich areas in the vaginal tissue. Such changes to collagen molecules can include, without limitation, changes to the structural organization and/or biomechanical properties of individual collagen fibers, as well as changes to the structural organization and/or biomechanical properties of higher order structures that are composed of or that comprise multiple collagen fibers. Non-limiting examples of remodeling processes include, e.g., activation of cell-signaling cascades, release of heat shock proteins, stimulation of cellular production and deposition of collagen into an extracellular space, or combinations thereof. In some embodiments, remodeling processes can include activation of cell signaling cascades that do not denature collagen molecules. In some embodiments, a remodeling process can involve deposition of new collagen molecules and/or changes to existing collagen molecules, e.g., changes to the structural organization and/or biomechanical properties of an existing collagen molecule. Remodeling processes that are induced by the subject methods generally result in one or more beneficial changes to the treated tissue. Such beneficial changes include, but are not limited to, a decrease is tissue looseness or laxity, an increase in sensation during coitus, an increase in hydration of the vaginal mucosa, or any combination thereof. Such beneficial changes also include decreasing the symptoms of urinary stress incontinence.

In some embodiments, the methods described above are applied via the use of an apparatus comprising a handpiece and a treatment tip, the handpiece further supported a by comprehensive upstream electronic system. In such embodiments, the treatment tip comprises a connector portion, which connects the tip to the handpiece, a midsection, typically narrowed, and a distal portion that comprises an energy delivery element. The treatment tip further comprises a housing that defines an internal space. The internal space accommodates a cooling system, with a lumen for conveying a refrigerating fluid, and nozzles, which are adapted to spray refrigerant on to the internal side of the energy delivery element thereby cooling it, such the cooled, in turn, cooling a genital mucosal epithelial surface on contact.

The types of energy delivery elements may include radiofrequency (RF), microwave, or ultrasound delivery embodiments. Some particular embodiments include capacitively-coupled RF electrodes, which may by monopolar or bipolar. Monopolar RF electrode-based embodiments may comprise a conductive pad to serve as a return electrode. Multi-polar RF-based embodiments may include one or more pairs of electrodes. The electrodes may further comprise thermal sensors that provide feedback control based on local temperature, and may further comprise EEROM chips that identify the treatment tip type or convey configuration parameters of the electrode to the hand piece, or to the larger electronic system.

The energy delivery element and the treatment tip as a whole are adapted to make optimal contact with the genital epithelial surface, when contact and capacitive coupling is occurring between the tip and an epithelial contact site. By optimal contact is meant a contact that best allows a delivery of energy into the target tissue that is broadly uniform across the surface of the contact site, notably without significant distortion along the edges of the contact site. Non-uniform delivery of energy does not result in consistent or effective treatment, and further may damage the mucosal epithelium. Non-limiting examples of adaptive configurations include a side-mounted configuration of the energy delivery element, the face of the energy delivery element being substantially parallel with respect to the linear axis of the treatment tip. Other non-limiting adaptive configurations include a narrowed mid-section of the tip proximal to the distal portion. This configuration allows the energy delivery element at the distal portion of the tip to project outward or forward from its surrounding support structure, thereby allowing the contact between the energy delivery element and the mucosal epithelium to be more accurate, deliberate, and visible (i.e., observable), and for the level of contacting pressure to be better controlled by the physician.

Further, the dimensions and configuration of the energy delivery element are adapted to optimize contact, particularly with the vaginal wall. The width of the energy delivery element is sufficient to engage the curved wall of the vagina in a manner that is sufficiently flat and parallel that the quality of contact across the face of the energy delivery element is substantially equal, without increased pressure, closer contact, or distortion along the edges of the element. Such a close contact allows for a uniform delivery of energy into the underlying target tissue. In some embodiments, the face of the energy delivery element is radially curved (with respect to the longitudinal axis of the tip) within the width of the element so as to create an arc of up to 30 degrees. Such curvature is also adapted to make parallel contact with the vaginal wall. In some embodiments, an element of about 1 cm width, per embodiments of the invention, requires about 10 or more contact sites to radially treat a 300-330 degree arc inside a vagina, thus a 30 degree arc provides for a good fit against the curve of the vaginal wall and thereby provides a uniform delivery of energy into the target tissue. In some embodiments, the contact sites can be anywhere along a 300 degree arc inside the vagina. In some embodiments, the contact sites can be anywhere along a 330 degree arc inside the vagina. In some embodiments, the contact sites can be anywhere along the entire 360 degree arc inside the vagina.

In some embodiments, the length of the energy delivery element is about 1 to about 3 cm in length, in other embodiments it may be as long as about 4 to 6 cm, or longer. This is a length well adapted to treating the lower aspect of the vagina, wherein treatment by the method comprises contacting the vaginal epithelium in a region that extends from the introitus inward to a position about 3 to 4 cm inward from the introitus. In some embodiments of the invention, the method can by practiced with a single row of parallel contact sites immediately inside the introitus. In other embodiments, the method may include deeper rows, or rows that overlap an initial row, while keeping the contact sites within the lower portion of the vagina.

Methods

Aspects of the invention include non-surgical (e.g., non-invasive) methods for treating urinary stress incontinence via the application of energy to a therapeutic zone of tissue (or target tissue) underlying the mucosal epithelium, while cooling the mucosal epithelium itself. The application of energy results in heating of the zone of tissue (or target tissue) underlying the mucosal epithelium to a desired temperature to induce tissue remodeling.

The term "vaginal tissue" is used in a broad sense herein to refer to any structures and/or tissues, including but not limited to the four layers described above, which form part of the internal or external female genitalia. The term "vaginal tissue" broadly includes, but is not limited to, the vaginal canal, as well as the vulva, which broadly includes the introitus, or external opening of the vaginal canal, and the surrounding structures, e.g., the labia, the clitoris, and the urinary meatus (or external urethral opening).

The term "treating" is broadly used herein to mean inducing one or more remodeling processes within a target tissue, e.g., a vaginal tissue. In some embodiments, a remodeling process can include changes to collagen molecules that are present within collagen-rich areas in the target tissues. Such changes to collagen molecules can include, without limitation, changes to the structural organization and/or biomechanical properties of individual collagen fibers, as well as changes to the structural organization and/or biomechanical properties of higher order structures that are composed of or that comprise multiple collagen fibers. Non-limiting examples of remodeling processes include, e.g., activation of cell-signaling cascades, release of heat shock proteins, stimulation of cellular production and deposition of collagen into an extracellular space, or combinations thereof. In some embodiments, remodeling processes can include activation of cell signaling cascades that do not denature collagen molecules. In some embodiments, a remodeling process can involve deposition of new collagen molecules and/or changes to existing collagen molecules, e.g., changes to the structural organization and/or biomechanical properties of an existing collagen molecule.

Remodeling processes that are induced by the subject methods generally result in one or more beneficial changes to the treated tissue. Such beneficial changes include, but are not limited to, a decrease is tissue looseness or laxity, an increase in sensation during coitus, an increase in hydration of the vaginal mucosa, a decrease in the symptoms of urinary stress incontinence or any combination thereof. Typically, the vaginal tissues that are treated in accordance with embodiments of the subject methods are those of women who have had one or more vaginal births, and whose vaginal tissues have been altered by giving birth. In particular, the tissues targeted for therapeutic intervention (FIG. 2) are the connective tissue layers such as the lamina propria or submocosa 104 and the muscularis 106 underlying the mucosal epithelium 100 of genital tissues. In some embodiments, the subject methods involve delivering energy to a vaginal tissue, but do not involve raising the temperature of the muscularis or adventitia. For example, in some embodiments, the subject methods involve delivering energy to vaginal tissues that are adjacent to the muscularis, but do not involve delivering energy into the muscularis itself. Particular features, or areas, of genital tissue (FIG. 1) having an epithelial surface include the vulva 126 and the vagina 122, and the introitus 114, the entrance to the vagina and a demarcation between the internal and external genitalia.

Aspects of the subject methods involve applying energy, e.g., to a vaginal tissue. In some embodiments, the energy is preferably radiant energy. Non-limiting examples of the types of energy that can be applied include radiofrequency (RF) energy, microwave and/or ultrasound energy.

In some embodiments, energy applied to the target tissue heats the tissue in the therapeutic zone to a temperature that ranges from about 38° C. to about 46° C., such as about 39° C., about 40° C., about 41° C., about 42° C., about 43° C., about 44° C., or about 45° C. The application of energy raises the temperature of the target tissue to a level that is therapeutic, i.e., to a temperature that causes remodeling, as described herein. In some embodiments, the therapeutic temperature may range between about 40° and 46° C. In some embodiments, the therapeutic temperature may range between about 40° and 42° C.

Role of Heat Shock Proteins

Raising the temperature of treated tissues to between about 42-46° C. as described throughout causes a biological response that results in a therapeutic effect on the tissue. This therapeutic effect includes remodeling of the tissue. The underlying biological processes contributing to this tissue remodeling are believed to be carried out (or at very least initiated in part) by the expression of heat shock proteins (HSPs) and the various cell signaling pathways these proteins are involved with. HSP expression levels are known to be elevated at the abovementioned temperatures and to play a role in collagen production (a component of tissue remodeling). For example, HSP47, a 47-kDa glycoprotein is elevated at 42° C. and higher temperatures, and is able to bind collagen. More specifically, HSP47 has been shown to be elevated in tissues at a temperature range from 30 to 45° C. (Sajjadi, Amir Yousef, Kunal Mitra, and Michael Grace. "*Expression of heat shock proteins 70 and 47 in tissues following short-pulse laser irradiation: assessment of thermal damage and healing.*" Medical engineering & physics 35.10 (2013): 1406-1414). Also, HSP47 is found in the endoplasmic reticulum (ER) of cells producing collagen type I and is actively involved in collagen type I biosynthesis (Verrico, A. K., and James V. Moore. "*Expression of the collagen-related heat shock protein HSP47 in fibroblasts treated with hyperthermia or photodynamic therapy.*" British journal of cancer 76.6 (1997): 719-724). Finally, downregulation of HSP47 has been shown to block the deposition of procollagens in the extracellular matrix, which decreases the level of collagens in fibrotic tissues (Kawasaki, Kunito, et al. "*Deletion of the collagen-specific molecular chaperone Hsp47 causes endoplasmic reticulum stress-mediated apoptosis of hepatic stellate cells.*" Journal of Biological Chemistry 290.6 (2015): 3639-3646).

The vagina is a fibromuscular tube, lined with stratified squamous epithelium that connects the external and internal organs of the female reproductive system. The vagina runs obliquely upwards and backwards at an angle of about 45 degrees between the bladder in front and the rectum and anus behind. In an adult female, the anterior wall is about 7.5 cm long and the posterior wall is about 9 cm long. The difference in length is due to the angle of insertion of the cervix through the anterior wall. More particularly, with regard to the vagina, methods in accordance with embodiments of the invention involve remodeling the lower portion of the vagina; the lower portion being that portion immediately inward from the introitus. Thus, according to some embodiments of the invention, the portion of the vagina to be treated is a region between the introitus and a position located no further than about 3 to 4 cm inward from the introitus. With regard to the circumferential aspects of the vagina, locations along the circumference of the vaginal wall may be assigned a clock position (see reference clock dial 136, in FIG. 1) such that the circumferential point closest to the urethra is at 12 o'clock. Using this orientation, methods in accordance with embodiments of the invention comprise treating vaginal tissues that are located at any clock position. In some embodiments, the subject methods involve treating vaginal tissues that are located along the 330 degree arc between 12:30 o'clock and 11:30 o'clock. Certain embodiments of the invention include treating the approximately 30 degree arc between 11:30 o'clock and 12:30 o'clock alongside the urethra, but avoid the area directly underneath the urethra.

The mucosal epithelium of vulvar tissue outside the vaginal canal includes the labia minora, or that portion of the vulva extending outward from the introitus to Hart's line, the boundary where mucosal epithelium and labial skin meet (FIG. 1). The mucosal epithelium and the skin, while contiguous, are embryologically and histologically distinct. The portions of the female genitalia that are covered by epithelium are also substantially defined by the bounds of the vestibule, which extends outward or down from the hymenal ring at the top of the vagina, radially beyond the introitus, including the portion of labia minora located within Hart's line 120. Target tissues in accordance with some embodiments include the connective tissue underlying these mucosal epithelial surfaces of the genitalia which, progressing down from the epithelial surface, are known as the lamina propria 104 and the muscularis 106 (FIG. 2), respectively (see, for example, Netter, Atlas of Human Anatomy, 4th edition, Saunders, 2006). The lamina propria includes a mixture of cell types that populate connective tissue, such as fibroblasts, and the muscularis is a layer of smooth muscle. Collagen is secreted or deposited into the extracellular space in these tissues by cells such as fibroblasts. These described target tissue layers below the mucosal epithelium overlay deeper tissues, including endopelvic fascia, which are not target tissues of the subject methods, but which may be bolstered and/or strengthened as a result of the subject methods.

In accordance with certain embodiments of the subject methods, treating the connective tissues underlying the mucosal epithelial surfaces does not substantially affect the mucosal epithelium itself because some embodiments of the methods involve protecting the mucosal epithelium by cooling it. The methods, as provided by embodiments of the invention, are non-invasive and non-ablative of genital tissue. The nature of the engagement between the apparatus and genital tissue is that of contacting a treatment tip to an epithelial surface of the genital tissue. Through such contact, the apparatus delivers energy to underlying tissue, resulting in an increase in the temperature of the underlying tissue, while protecting the mucosal epithelial surface by cooling it.

In a particular embodiment, a method for treating vaginal tissue through the use of an RF energy source is provided, wherein the RF energy passes through the vaginal or vulvar mucosal epithelial tissue and is delivered to the respective underlying layers of the therapeutic zone. Other embodiments may make use of other forms of energy, such as microwave or ultrasound energy. Impedance through mucosal epithelium is lower than through skin, thus, less energy is required when treating mucosal epithelium to cause a desired increase in temperature than would be required were skin being treated.

As described herein, the application of energy to a target tissue causes an increase in the temperature in the therapeutic zone. Without being bound by any particular theory, the increase in temperature in the therapeutic zone can cause, e.g., tissue remodeling, which may include activation of cell signaling cascades such as, e.g., heat shock protein-mediated cascades, without denaturing collagen. In some embodiments, the application of energy to a target tissue results in deposition of new or nascent collagen by cells of the target tissue, as part of a biological process that may take place over the course of days, weeks or months following the procedure.

As provided above, aspects of the invention involve treating of vaginal tissue, which induces remodeling of the vaginal tissue. In such embodiments, remodeling of the vaginal tissue can result in, e.g., activation of cell-signaling cascades, release of heat shock proteins, stimulation of cellular production and deposition of collagen into an extracellular space, or combinations thereof. In some embodiments, remodeling processes can include activation of cell signaling cascades that do not denature collagen molecules. In some embodiments, a remodeling process can involve deposition of new collagen molecules and/or changes to existing collagen molecules, e.g., changes to the structural organization and/or biomechanical properties of an existing collagen molecule. A longer-term biological consequence of the subject methods may include a process in which there is an increase in a rate of cellular production and deposition of collagen into the extracellular space. Without being bound to any particular theory, both types of responses, the near immediate response of pre-existing collagen, and the longer-term increased amount of collagen, are understood to contribute to an overall beneficial effect from remodeling of the target tissue.

The result of treating vaginal tissue is accordance with embodiments of the subject methods is that the remodeled genitalia assumes a rejuvenated form, a conformation of the genitalia as they were before having undergone vaginal trauma, childbirth or aging. Vaginal tissue that has been rejuvenated via application of the subject methods, by virtue of remodeling of the tissue, may provide greater pelvic floor support, leading to potentially greater sexual satisfaction for a woman with such remodeled genitalia and for her sexual partner.

Aspects of the invention include methods for creating a reverse thermal gradient that uses one or more RF electrodes to convey energy that increases the temperature of one or more target tissues within a therapeutic zone, and a mechanism to cool the mucosal epithelial surface above the targeted underlying layers. Cooling the mucosal epithelial surface serves to protect it from potentially damaging effects of increased temperature that would occur in the absence of cooling. The mucosal epithelial surface is thus a conduit for energy passing through to underlying layers, but the energy does not manifest in the form of increased temperature at the epithelial surface. As such, the epithelium itself is not damaged or substantially modified by the subject methods. Such protection from increased temperature may derive both from the heat-sink aspect of a cooled body, as well as an increase in tissue impedance that is associated with cooled tissue.

In some embodiments, an apparatus comprising a cooling mechanism is used to carry out the subject methods. In such embodiments, the cooling mechanism of the apparatus includes a lumen adapted to accommodate a cooling fluid conveyed to nozzles, which cool the energy delivery element of a treatment tip of the apparatus. Some embodiments of the methods thus provide for contacting a contact site on a genital epithelial surface, the tip being adapted or configured to both cool the surface epithelium and to deliver energy to the underlying tissue. The cooling fluid cools the treatment tip of the apparatus, as provided by embodiments of the invention; in turn, the surface of the cooled treatment tip cools the surface of the mucosal epithelium that the treatment tip contacts. As provided in some embodiments, the epithelial surface may be cooled to a temperature that ranges from about 0° C. to about 10° C., such as about 1° C., about 2° C., about 3° C., about 4° C., about 5° C., about 6° C., about 7° C., about 8° C., or about 9° C. As energy from the tip passes through the mucosal epithelial surface, the underlying soft tissue may be heated to a temperature that ranges from about 38° C. to about 46° C., such as between about 40° C. to about 46° C., or between about 40° C. to about 42° C. in the therapeutic zone. Thus, a reverse thermal gradient is created, with a lower temperature at the mucosal epithelium, and a higher temperature in the underlying tissue.

In some embodiments, a method includes feedback control mechanisms to control the energy delivery such that temperature does not exceed a predetermined level. As provided by embodiments of the apparatus, the feedback is provided to RF delivery by thermal or impedance sensors. In other embodiments, the method may be controlled by delivering a predetermined total of amount of energy. In some embodiments the method may be controlled by delivering an amount of energy within a predetermined amount of time.

More specifically, within a target tissue of the invention, a therapeutic zone may be defined, where the energy is particularly focused and causes a temperature increase to a threshold temperature that is sufficient to result in tissue remodeling. Such a therapeutic zone may be centered at a particular depth below the epithelium, and the therapeutic zone may have a particular range of depth. It may, for example, be broadly distributed across the full range of the lamina propria and muscularis, or it may occupy a relatively flat zone. In some embodiments, cooling is allowed to proceed into the target tissue itself, below the epithelial surface, to form a cold-protected tissue zone. The cooling of a portion of the target tissue may have an effect on the therapeutic zone, such that the depth and range of the therapeutic zone may be modulated or shifted with respect to where it would be, absent such cooling of a portion of the target tissue. If cooling penetrates to a given level in the target tissue to create a cold-protected zone, for example, the therapeutic zone may be pushed deeper into the target tissue.

In some embodiments, a method involves surface cooling coincident with the time that energy is being delivered to impact the underlying tissue. In some embodiments, in addition to cooling the surface while raising the temperature of the underlying tissue, a method includes a period of cooling before the application of energy. In other embodiments, a method includes a period of cooling after the application of energy. In still other embodiments, a method includes cooling both before and after the application of energy.

Figure 2:
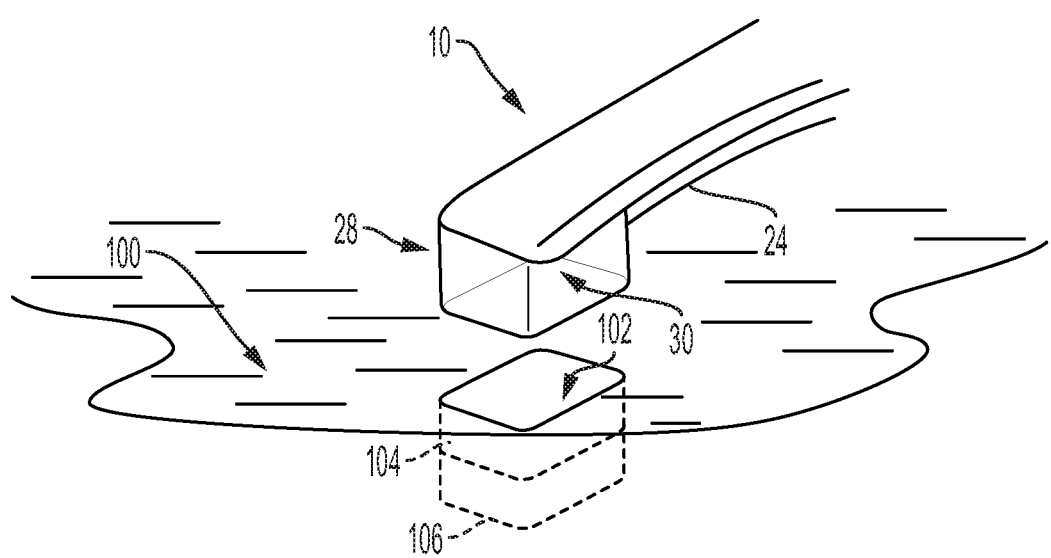
FIG. 2 shows a treatment tip contacting a genital epithelial mucosal surface and the underlying target tissue including the lamina propria and the muscularis.

As shown in FIG. 2, a treatment tip 10 of an apparatus contacts a contact site 102 on the mucosal epithelium 100, and such contact creates a site on the epithelium corresponding to the surface area within the outline of the profile of the treatment tip. FIG. 2 shows the distal end 28 of the tip, with the energy delivery element 30 (shown by dotted lines) facing toward the mucosal epithelium. Also shown below the contact site 102 (with dotted lines) are target tissue layers, the lamina propria 104 and the muscularis 106. In some embodiments of the invention, a method includes making contact with the epithelium, delivering energy, and then moving the treatment tip to another contact site, and delivering energy there. A procedure, such as would take place in a visit to a medical office, would typically include a circumferential sequence of contacting the epithelium within the vagina and/or contacting other sites outside the vagina. During the same procedure, the treatment tip may be returned to the same contact point multiple times. The circumference of the lower portion of an unfolded vagina, gently stretched as it is during the practice of the subject methods, is approximately 12 cm in length. Accordingly, with a treatment tip of about 1 cm in width, a series of about 10 contact sites allows completion of a 330 degree arc of the circumference, between the 12:30 and 11:30 o'clock positions. These dimensional considerations underlie the rationale for some embodiments of the subject methods wherein the surface of the energy delivery element has a curvature of about 30 degrees, each contact site accounting for about 10% of the 330 degree arc.

In accordance with some embodiments of the subject methods, a "pulse" of energy (or "energy pulse") is applied to target tissues at a plurality of target locations. In some embodiments, target locations can be adjacent to one another, separated by a predefined distance, or overlapping. As used interchangeably herein, the terms "target tissue location" and "target location" refer to a target tissue as well as one or more tissue layers that may be located above (e.g., a surface tissue layer) and below the target tissue. Delivery of energy in accordance with the subject methods causes the target tissue to increase in temperature to a desired therapeutic temperature. In some embodiments, each pulse can include a period of cooling of the target tissue which can follow, precede or occur concurrently with the application of energy. The terms "pulse" and "energy pulse" are used interchangeably throughout. According to some embodiments, a pulse delivers energy to a target tissue. Non-limiting examples of energy include radiofrequency (RF) energy, microwave energy, and ultrasound energy.

Delivering energy to a target tissue in accordance with embodiments of the subject methods raises the temperature of the target tissue to a therapeutic temperature. In some embodiments, the therapeutic temperature can be as high as about 46° C. The therapeutic temperature in some embodiments may be as high as about 45° C. In some embodiments, the therapeutic temperature may range between about 38° and about 46° C. In some embodiments, the therapeutic temperature may range between about 40° and about 46° C. In some embodiments, the therapeutic temperature may range between about 40° and about 42° C.

In some embodiments, each pulse can include application of energy for a period of time that ranges between about 1 and about 5 seconds in length, and more preferably up to about 2 seconds in length. In some embodiments, an initial cooling phase can have a duration of up to about 0.5 seconds in length. In some embodiments, a follow-up cooling phase can have a duration that ranges from about 2 up to about 4 seconds in length.

In some embodiments, multiple pulses are delivered in a consecutive manner to one target location. In some embodiments, multiple pulses are delivered to one target location, and each of the pulses is separated by a period of time between pulses. In such embodiments, the period of time between pulses can range between about 0.5 minutes to about 4 minutes, and more preferably between 1 minute and 2 minutes, and more preferably about 2 minutes. In some embodiments, multiple pulses are delivered in a consecutive manner and the application of the individual pulses is carried out via a combination of approaches with some pulses being applied in a consecutive manner with little or no time between pulses, and other pulses being separated by a period of time between pulses.

In some embodiments, a treatment protocol includes a plurality of pulses delivered to a plurality of target locations around the vaginal canal. In such embodiments, each of the plurality of pulses is applied to a plurality of target locations around the vaginal canal in a predetermined order. This plurality of pulses applied to a plurality of target locations around the vaginal canal in a predetermined order is referred to as a "pass" or "cycle" or "energy delivery pass" or "energy delivery cycle" (used interchangeably throughout). In some embodiments, a treatment protocol includes 1, 2, 3, 4, 5 or more passes. In some embodiments, each pass is completed consecutively with little or no lag time, while in other embodiments there is a predetermined lag time between each pass. In some embodiments, a total of about 220 pulses are applied to a plurality of target locations around the vaginal canal over the course of 1, 2, 3, 4, 5 or more passes during a single treatment session. According to some embodiments, one or more of the plurality of pulses delivers energy to a target tissue. Non-limiting examples of energy include radiofrequency (RF) energy, microwave energy, and ultrasound energy.

In some embodiments, a plurality of target locations are divided among predetermined quadrants around the vaginal canal. In such embodiments, a first quadrant is from 12 o'clock to 3 o'clock, a second quadrant is from 3 o'clock to 6 o'clock, a third quadrant is from 6 o'clock to 9 o'clock, and a fourth quadrant is from 9 o'clock to 12 o'clock, where the urethra is located at 12 o'clock. In such embodiments, each quadrant can have 1, 2, 3, 4, 5, 6 or more target locations.

According to some embodiments of the invention, the energy pulses can be applied to a plurality of target tissue locations as illustrated in FIGS. 3A-3D. FIGS. 3A-3D show four non-limiting example schematics, with each of FIGS. 3A-3D representing a schematic showing a cross-section of the vaginal canal 302 and urethral opening 304 and targeted tissue locations on the vaginal canal. Also shown for orientation is the hymen 306, and the cervix 308. In such embodiments, the circumference of the vaginal canal is divided into four quadrants with a first quadrant from a 12 o'clock position to a 3 o'clock position, a second quadrant from the 3 o'clock position to a 6 o'clock position, a third quadrant is from the 6 o'clock position to a 9 o'clock position, and a fourth quadrant is from the 9 o'clock position to the 12 o'clock position, and where the urethra of the subject is located at the 12 o'clock position.

Figure 3A:
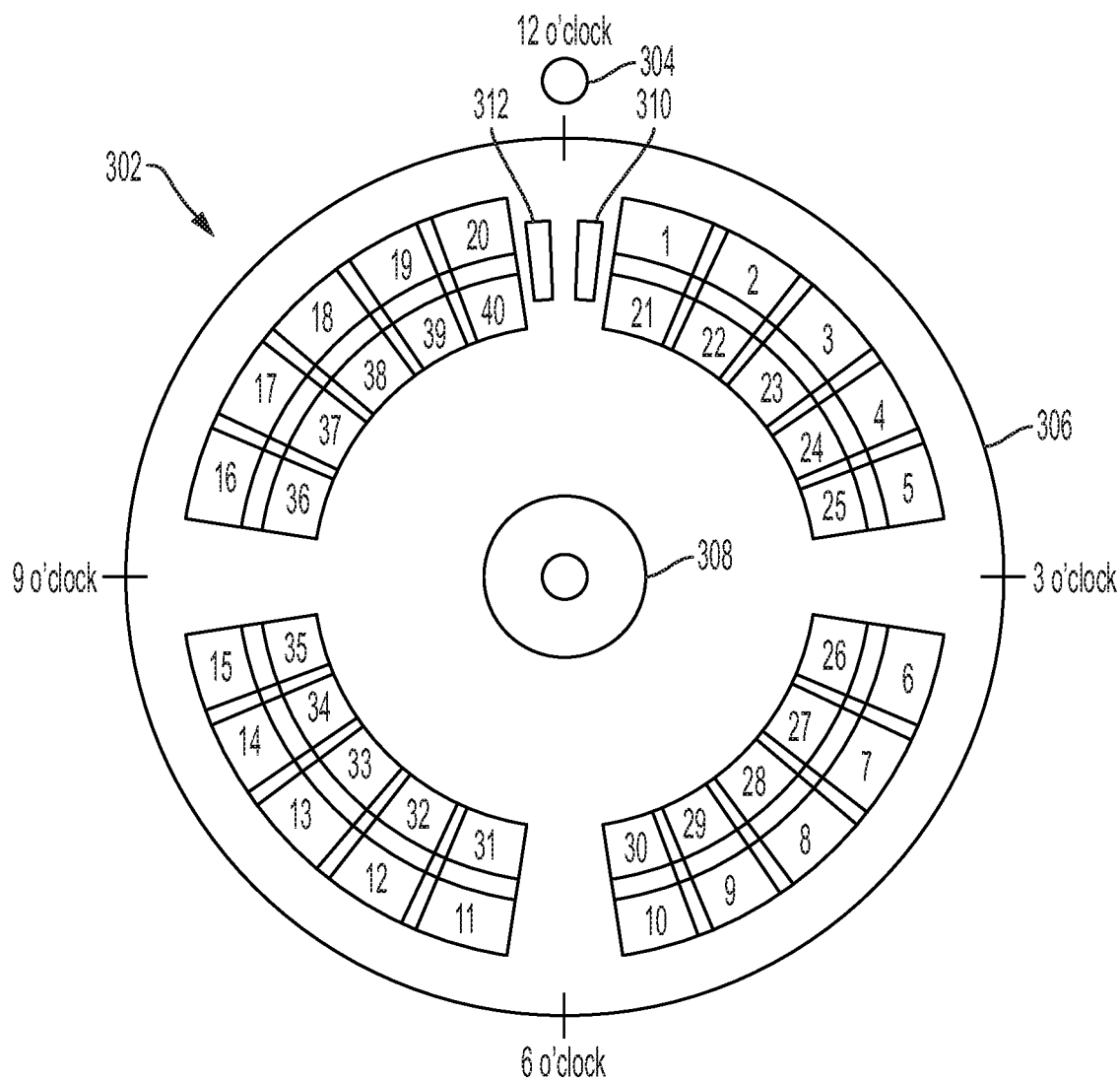
FIGS. 3A-3D are illustrations of example mapping grids depicting a plurality of target tissue locations according to some embodiments of the invention.
Figure 3B:
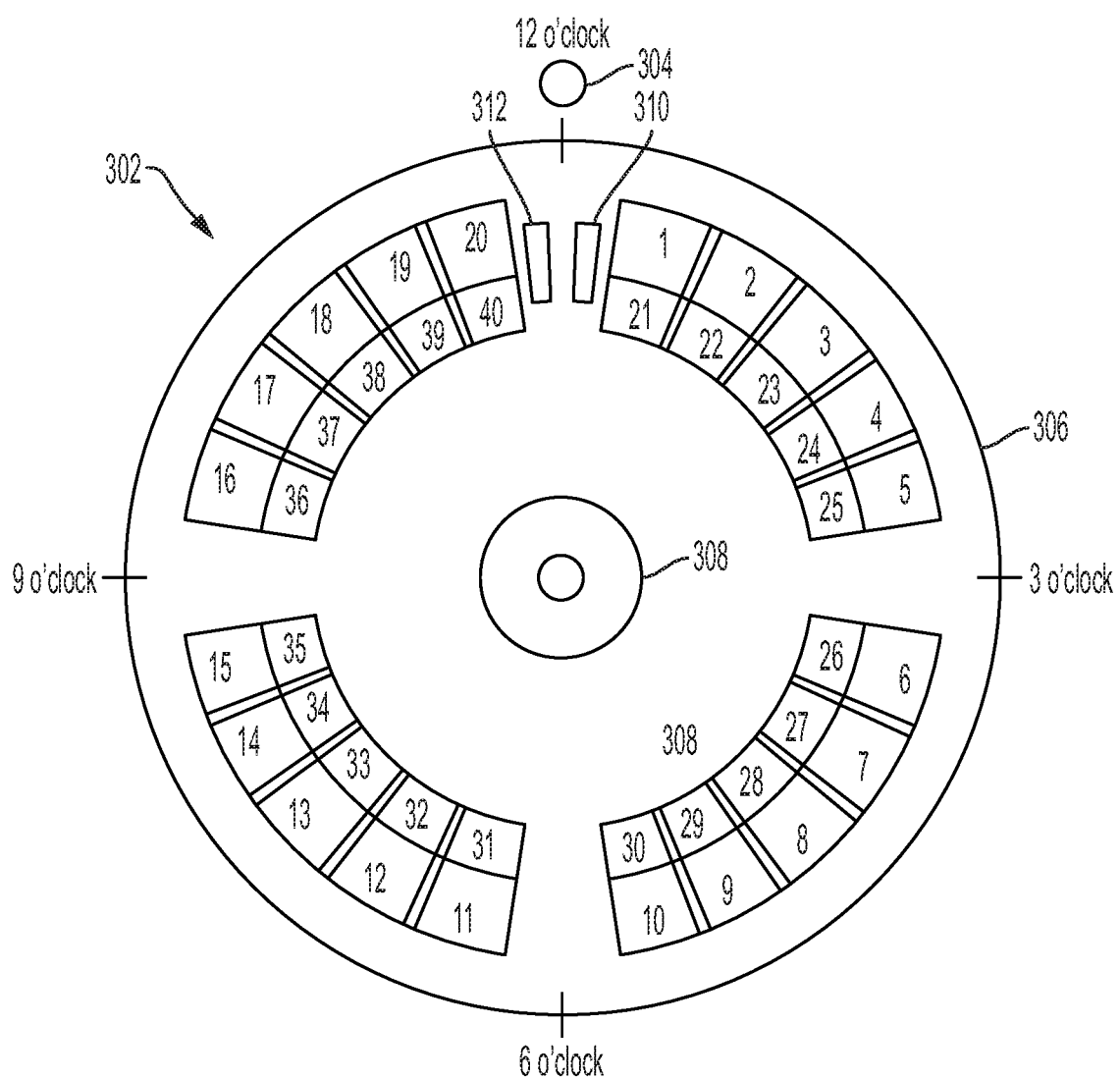
Figure 3C:
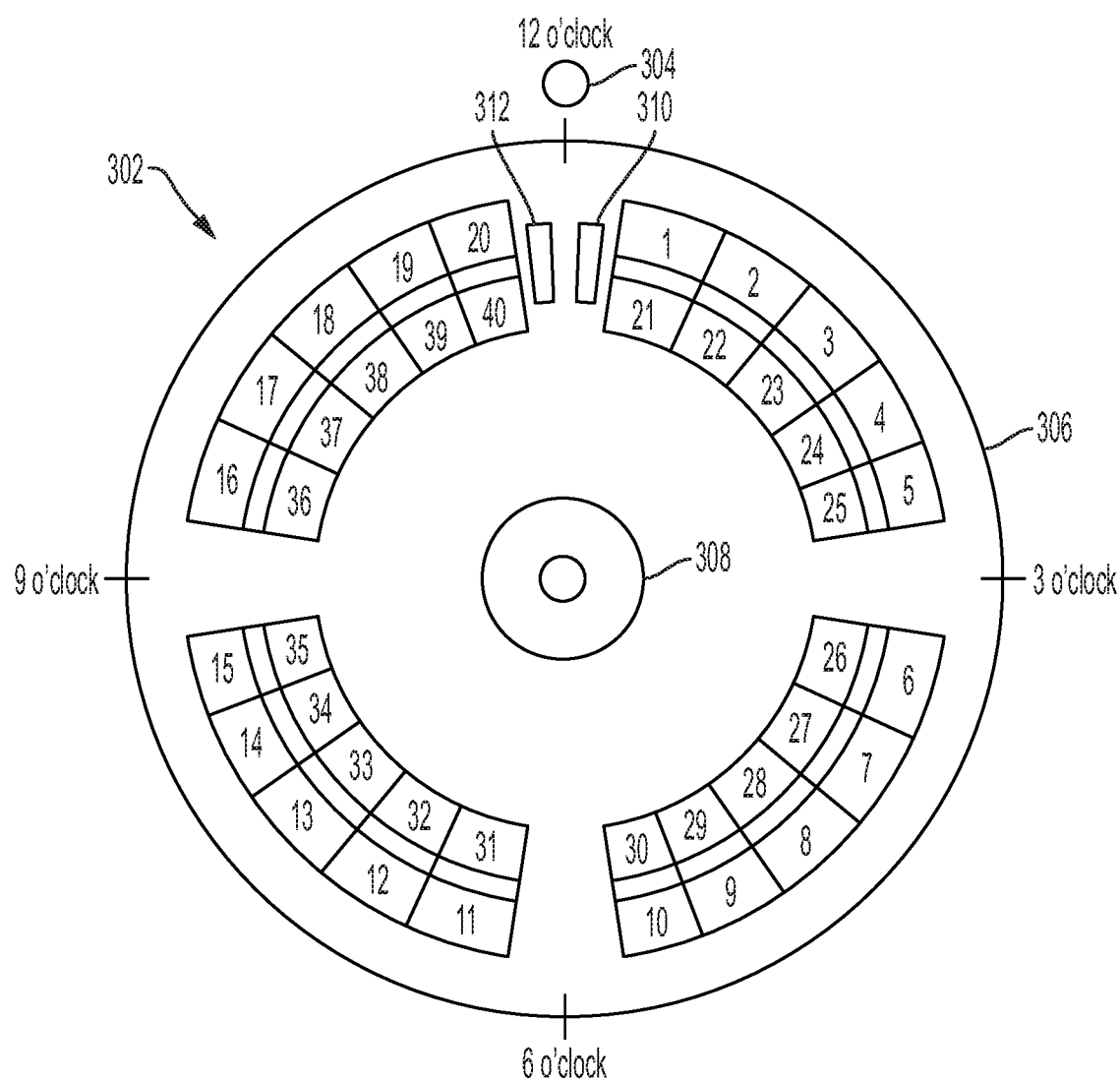
Figure 3D:
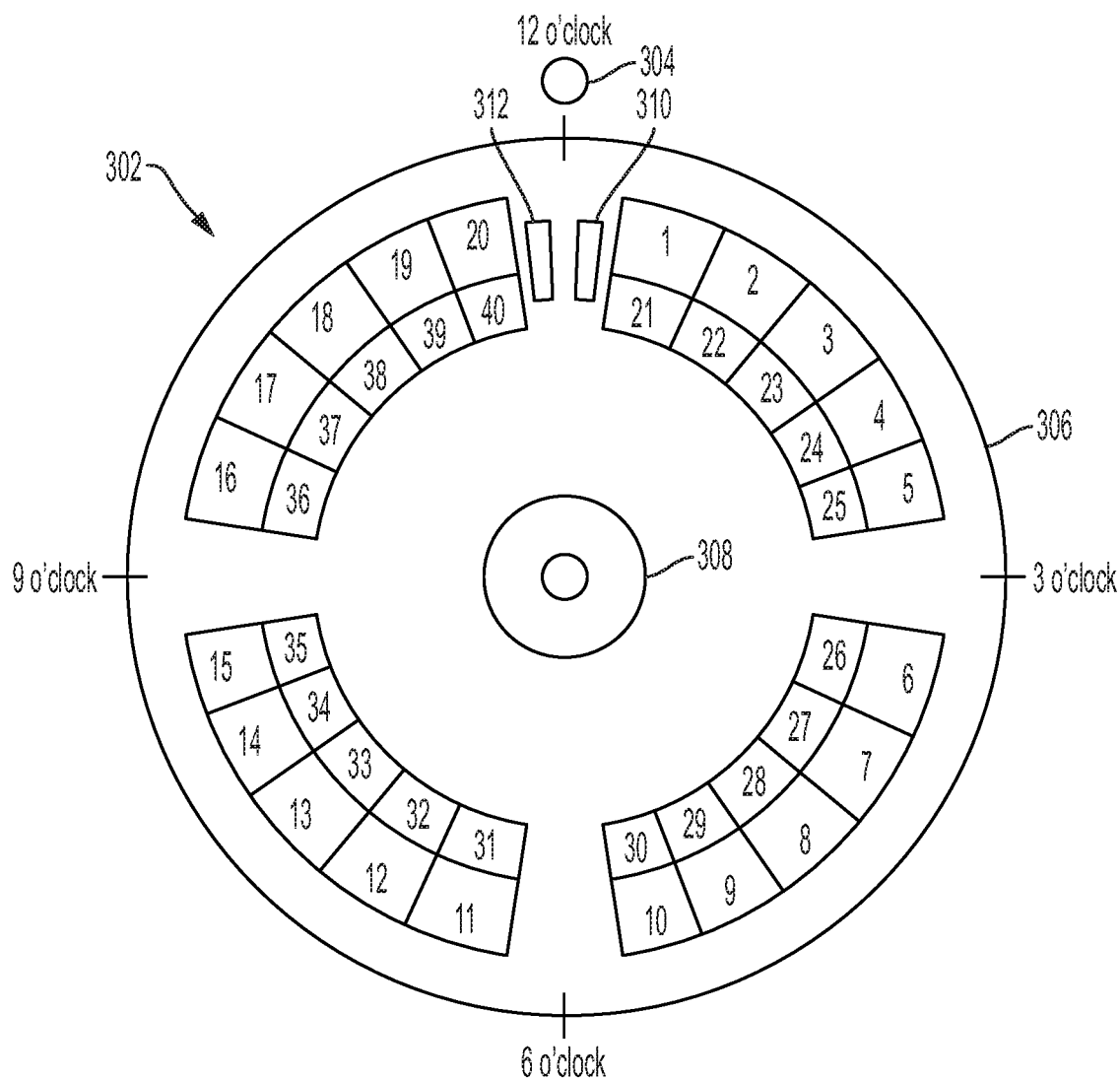

In FIGS. 3A-3D, each tissue target location is depicted by numbers 1-40. In FIGS. 3A-3D, tissue target locations 1-20 are proximal to the introitus, while tissue target locations 21-40 are located deeper into the vaginal canal and are proximal to tissue target locations 1-20. In some embodiments the tissue target locations overlap at least partially with adjacent tissue target locations and with tissue target locations located above or below as seen in FIG. 3A. In some embodiments the tissue target locations overlap at least partially with adjacent tissue target locations as seen in FIG. 3B. In some embodiments the tissue target locations overlap at least partially with tissue target locations located above or below as seen in FIG. 3C. In some embodiments the tissue target locations do not overlap with adjacent tissue target locations or with tissue target locations located above or below as seen in FIG. 3D. In some embodiments, tissue target locations located alongside the urethra 310, 312 are also treated. Embodiments of the invention are not limited to the schematics and tissue target locations depicted in FIGS. 3A-3D.

As summarized above, in some embodiments, a given treatment area is treated during a single procedure during an office visit. Aspects of the methods further include repetitions of such procedures, typically on another day, when the effects of the previous procedure may be evaluated. From such evaluation, judgment may be made with regard to re-treating a particular previously-treated area, or proceeding to treat other areas. Thus, as provided by embodiments of the method, one or more procedures during follow-up visits may variously include treating the same treatment area, treating an entirely different treatment area, or treating an overlapping treatment area, partially the same as the previous area, and partially different.

Other variations of treatment tip design and associated methods can be employed to achieve the objectives of the invention without departing from the scope of the invention, as will be appreciated by those skilled in the art. For example, the shape and dimensions of the treatment tip can also be adjusted, as desired, to enhance the effectiveness of the treatment, taking into consideration physiological and anatomical information.

While various embodiments of the present invention have been shown and described herein, those skilled in the art will understand that such embodiments are provided by way of example only. Although the description has offered various theories, such theories have been offered simply as possible theories of how the invention works and as an aid in describing the invention; however, it should be understood that such theories and interpretation do not bind or limit the claims with regard to tissue remodeling brought about by the practice of the invention. Numerous variations, changes, and substitutions will occur to those skilled in the art without departing from the invention. It should be understood that various alternatives to the embodiments of the invention described herein may be employed in practicing the invention. It is intended that the scope of the invention, methods and structures within the scope of the invention includes equivalents.

An embodiment of the invention relates to a method for remodeling tissue of the vagina by the application of energy to induce a specific cellular response. The method generally includes the steps of: non-invasively delivering energy to a subsurface region of a target location to a temperature for a period of time sufficient to induce specific cellular changes which lead to remodeling of the target region.

An embodiment of the invention relates to a method for remodeling tissue of the vagina by the application of energy to induce a specific cellular response as described above, where the step of non-invasively delivering energy further includes heating the target tissue to at least one of a predetermined temperature for a predetermined period of time to induce remodeling of the target tissue.

An embodiment of the invention relates to a method for remodeling tissue of the vagina by the application of energy to induce a specific cellular response as described above, where the method further includes the step of cooling the target location.

An embodiment of the invention relates to a method for remodeling tissue of the vagina by the application of energy to induce a specific cellular response as described above, where the step of non-invasively delivering energy results in heating the target tissue to as high as about 46° C., or between about 38° and 46° C., or between about 40° and 46°, or between about 40° and 42° C.

An embodiment of the invention relates to a method for remodeling tissue of the vagina by the application of energy to induce a specific cellular response as described above, where the step of non-invasively delivering energy involves delivering at least one of radiofrequency energy, microwave energy, laser energy, or ultrasound energy.

An embodiment of the invention relates to a method for remodeling tissue of the vagina by the application of energy to induce a specific cellular response as described above, where the period of time sufficient to induce remodeling of the subsurface region is between 1 second to 5 seconds.

An embodiment of the invention relates to a method for remodeling tissue of the vagina by the application of energy to induce a specific cellular response as described above, where the step of non-invasively delivering energy further results in heating a submucosal region of a vaginal tissue.

An embodiment of the invention relates to a method for remodeling vaginal tissue by the application of energy to induce a specific cellular response as described above, where a step of cooling one or more tissues and/or tissue layers (e.g., a mucosal epithelial surface of a vaginal tissue, a mucosal layer of vaginal tissue) of the target location is included.

An embodiment of the invention relates to a method for remodeling tissue of the vagina by the application of energy to induce a specific cellular response as described above, where the step of cooling one or more tissues and/or tissue layers includes contacting an epithelial tissue layer of the target tissue with a treatment tip, the treatment tip including a cooling mechanism.

An embodiment of the invention relates to a method for remodeling tissue of the vagina by the application of energy to induce a specific cellular response as described above, where the step of cooling one or more tissues and/or tissue layers includes cooling an epithelial tissue layer to a temperature between 0° C. and 10° C.

An embodiment of the invention relates to a method for remodeling tissue of the vagina by the application of energy to induce a specific cellular response as described above, where the remodeling includes at least one of contracting the target tissue, bolstering the target tissue, tightening collagen-rich sites in the target tissue, releasing heat shock proteins within the target tissue, initiating one or more cellular signaling cascades within the target tissue, or any combination thereof.

An embodiment of the invention relates to a method for remodeling tissue of the vagina by the application of energy to induce a specific cellular response as described above, where the step of non-invasively delivering energy includes applying energy to a plurality of target locations located around the vaginal canal between 12:30 o'clock and 11:30 o'clock, where a urethra of a subject is 12 o'clock.

An embodiment of the invention relates to a method for remodeling tissue of the vagina by the application of energy to induce a specific cellular response as described above, where the applied radiofrequency energy penetrates to ~5 mm deep in the treated tissue area. In some embodiments, the applied radiofrequency energy penetrates to a depth of between 3 mm-5 mm in the treated tissue area.

An embodiment of the invention relates to a method for remodeling tissue of the vagina by the application of energy to induce a specific cellular response as described above, where therapeutic treatment dose is about treatment dose of about 90 J/cm$^2$.

EXAMPLES

Example 1

A method for treating urinary stress incontinence in a subject includes the following treatment protocol:

A subjects is treated with an active treatment tip (delivering 90 J/cm$^2$ of RF energy).

A total of 220 pulses are applied during a treatment procedure. The treatment area is divided into quadrants of the vaginal introitus, with the area directly beneath the urethra excluded. Two treatment tips are used during the procedure, with one hundred ten (110) pulses programmed on each treatment tip.

First Treatment Tip.

A first set of 100 pulses are applied to the area just behind the hymenal ring using the quadrant approach. Each quadrant is treated with five consecutive passes of five locations of pulses for a total of 25 pulses per quadrant. The pulses are applied in a clockwise fashion with an overlap of approximately 0.5 cm. Once a quadrant is fully treated with 25 pulses the next quadrant is treated. This process continues until all four quadrants are treated. Next, the treatment tip is advanced the length of the electrode of the treatment tip (approximately 2 cm) into the vaginal canal and the 10 remaining pulses on the treatment tip are applied in an alternating manner between the right and left side of the urethra. The first treatment tip is then removed from the handpiece and replaced with the second treatment tip.

Second Treatment Tip.

A second set of 100 pulses are applied in a similar fashion to the first set but with the proximal edge of the treatment tip window positioned 1.0 cm behind the hymenal ring. This provides approximately a 1.0 cm overlap of treatment pulses. Similar to the process with the first treatment tip above, each quadrant is treated with five consecutive passes of five locations of pulses for a total of 25 pulses per quadrant. The pulses are applied in a clockwise fashion with an overlap of approximately 0.5 cm. Once a quadrant is fully treated with 25 pulses the next quadrant is treated. This process continues until all four quadrants are treated. Next, the second treatment tip is advanced the length of the electrode of the treatment tip (approximately 2 cm) into the vaginal canal and the 10 remaining pulses on the treatment tip are applied in an alternating manner between the right and left side of the urethra.

In this example, a cryogen-cooled monopolar RF device with a reverse thermal gradient at the vaginal introitus was used to elevate tissue temperature to cause cellular changes that rejuvenate tissue. After receiving the outcome temperatures, it is apparent that the likely mechanism of action is the activation of heat shock proteins which causes a protein stress response along with the formation of precollagen by collagen producing cells and collagen binding agents. The RF energy allows for the heat shock protein effect to occur in the deeper tissues and the reverse thermal gradient protects the mucosal layer of tissue, closest to the site of RF energy administration from the device. The effect was observed by applying at least five cycles of RF energy in one tissue location at the vaginal introitus, which allows for enough energy to raise the tissue temperature without causing cellular damage.

Scientific literature supports the theory that temperatures lower than 45 to 55° C. can actually result in a heat shock protein response that leads to favorable collagen changes. Such lower temperatures are achieved with the instantly disclosed RF device at depths within the submucosa that provide support to the vaginal canal. In addition, the tissue temperatures that are achieved from the subject methods are well below those that would cause cellular damage. Thus, the device disclosed herein is a safe and effective treatment for a number of women's health indications with a unique method of delivery and mechanism of action.

Example 2

Figure 4:
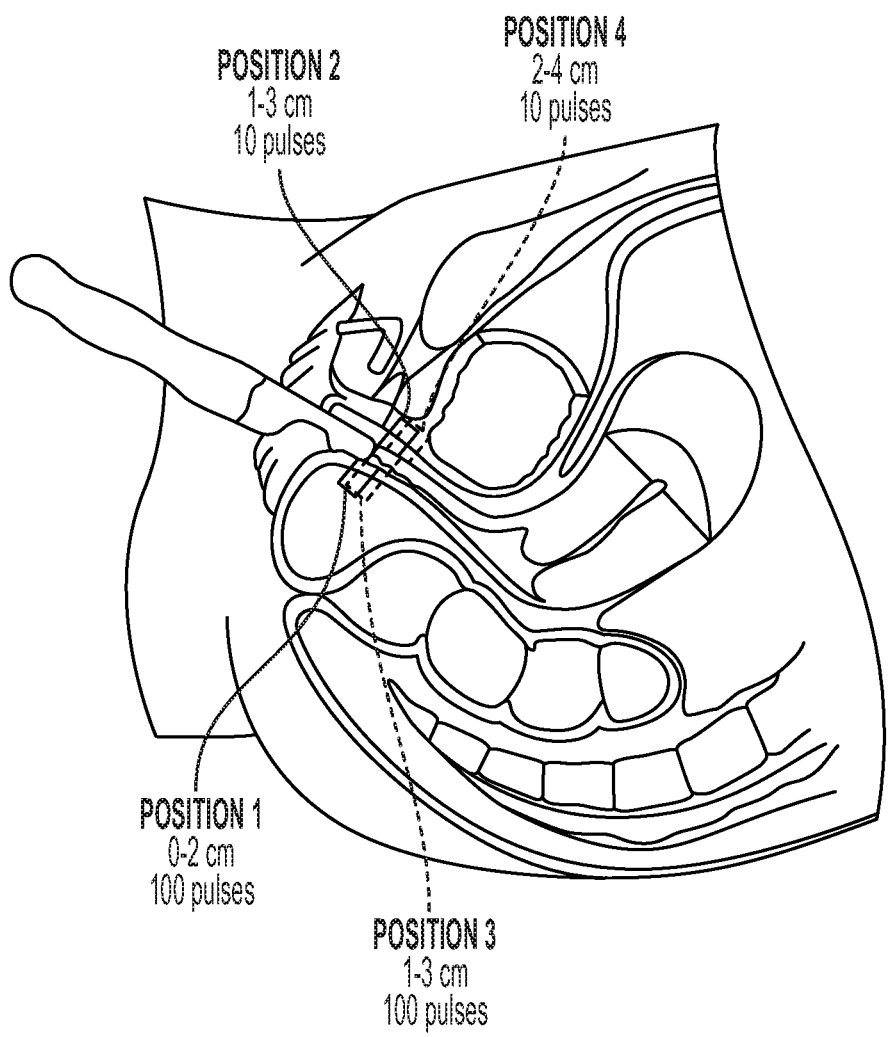
FIG. 4 is a treatment diagram according to an embodiment of the invention.

A method for treating urinary stress incontinence in a subject includes the following treatment protocol, and is also outlined in FIG. 4:

A subject is placed on an examination table in a dorsal lithotomy position. The vagina, perineum, and peri-anal area will be cleansed using a sterile saline wipe. Coupling fluid will be applied to the entire treatment area and the treatment tip to ensure safe RF transfer and cooling effectiveness. The coupling fluid acts as a conductor and skin protectant and is not a lubricant. No substitutes should be used for the coupling fluid and no lubricants should be used for the procedure. Additional coupling fluid will be reapplied throughout the treatment to ensure appropriate transfer of RF energy.

A subject is treated with an active treatment tip (delivering 90 J/cm2 of RF energy).

The treatment area is divided into quadrants of the vaginal introitus with the area directly beneath the urethra excluded. One hundred and ten (110) pulses are programmed on each treatment tip. Two (2) treatment tips per subject will used to administer the protocol.

First Treatment Tip:

Position 1: 0-2 cm beyond hymenal ring (100 pulses). The treatment tip placement is beyond hymenal ring: proximal edge 0 cm, distal edge 2 cm. The first set of 100 pulses is applied to the area just behind the hymenal ring using the quadrant approach. Each quadrant is treated with 5 consecutive passes of 5 locations of pulses for a total of 25 pulses/quadrant. Pulses are applied in a clockwise fashion with an overlap of ~0.5 cm. Once a quadrant was fully treated with 25 pulses, the next quadrant will be treated, until all 4 quadrants are treated. The treatment area should avoid the area overlying the urethra, by using the urethral sparing window and avoiding treatment between 11 o'clock and 1 o'clock.

Position 2: 1-3 cm beyond hymenal ring (10 pulses). The treatment tip placement is beyond hymenal ring: proximal edge 1 cm, distal edge 3 cm. The second depth of treatment involves positioning the proximal edge of the treatment tip window ~1 cm behind the hymenal ring. Five pulses are applied directly to the right of the urethra and five pulses are applied directly to the left of the urethra observing the urethral sparing window between 11 o'clock and 1 o'clock.

Second Treatment Tip:

Position 3: 1-3 cm beyond hymenal ring (100 pulses), Position 3 is ~1 cm overlapped with Position 1. The treatment tip placement beyond hymenal ring: proximal edge 1 cm, distal edge 3 cm (there should be ~1 cm overlap between Position 1 and Position 3). The third set (Position 3) of pulses (which comprises 100 pulses) are applied in a similar fashion to Position 1, but at ~1 cm deeper than Position 1. This provides an ~1 cm overlap of treatment pulses. The treatment area should avoid the area overlying the urethra, by using the urethral sparing window and avoiding treatment between 11 o'clock and 1 o'clock.

Position 4: 2-4 cm beyond hymenal ring (10 pulses), Position 4 is ~1 cm overlapped with Position 2. The treatment tip placement is beyond hymenal ring: proximal edge 2 cm, distal edge 4 cm (there should be ~1 cm overlap between Position 2 and Position 4). The fourth depth of treatment (Position 4) is applied in a similar fashion to the Position 2, but with the proximal edge of the treatment tip window positioned ~2 cm behind the hymenal ring. Five pulses are applied directly to the right of the urethra and five pulses are applied directly to the left of the urethra observing the urethral sparing window between 11 o'clock and 1 o'clock.

The treatment is completed when a total of 220 pulses have been applied.

Example 3

A method for treating urinary stress incontinence in a subject includes the following treatment protocol:

A subjects is treated with an active treatment tip (delivering 90 J/cm² of RF energy).

A total of 220 pulses are applied during a treatment procedure. The treatment area is divided into quadrants of the vaginal introitus, with the area directly beneath the urethra excluded. A single treatment tip is used during the procedure.

A first set of 100 pulses are applied to the area just behind the hymenal ring using the quadrant approach. Each quadrant is treated with five consecutive passes of five locations of pulses for a total of 25 pulses per quadrant. The pulses are applied in a clockwise fashion with an overlap of approximately 0.5 cm. Once a quadrant is fully treated with 25 pulses the next quadrant is treated. This process continues until all four quadrants are treated. Next, the treatment tip is advanced the length of the electrode of the treatment tip (approximately 2 cm) into the vaginal canal and the 10 remaining pulses on the treatment tip are applied in an alternating manner between the right and left side of the urethra. The first treatment tip is then removed from the handpiece and replaced with the second treatment tip.

A second set of 100 pulses are applied in a similar fashion to the first set but with the proximal edge of the treatment tip window positioned 1.0 cm behind the hymenal ring. This provides approximately a 1.0 cm overlap of treatment pulses. Similar to the process above, each quadrant is treated with five consecutive passes of five locations of pulses for a total of 25 pulses per quadrant. The pulses are applied in a clockwise fashion with an overlap of approximately 0.5 cm. Once a quadrant is fully treated with 25 pulses the next quadrant is treated. This process continues until all four quadrants are treated. Next, the treatment tip is advanced the length of the electrode of the treatment tip (approximately 2 cm) into the vaginal canal and the 10 remaining pulses on the treatment tip are applied in an alternating manner between the right and left side of the urethra.

In this example, a cryogen-cooled monopolar RF device with a reverse thermal gradient at the vaginal introitus was used to elevate tissue temperature to cause cellular changes that rejuvenate tissue. After receiving the outcome temperatures, it is apparent that the likely mechanism of action is the activation of heat shock proteins which causes a protein stress response along with the formation of precollagen by collagen producing cells and collagen binding agents. The RF energy allows for the heat shock protein effect to occur in the deeper tissues and the reverse thermal gradient protects the mucosal layer of tissue, closest to the site of RF energy administration from the device. The effect was observed by applying at least five cycles of RF energy in one tissue location at the vaginal introitus, which allows for enough energy to raise the tissue temperature without causing cellular damage.

Scientific literature supports the theory that temperatures lower than 45 to 55° C. can actually result in a heat shock protein response that leads to favorable collagen changes. Such lower temperatures are achieved with the instantly disclosed RF device at depths within the submucosa that provide support to the vaginal canal. In addition, the tissue temperatures that are achieved from the subject methods are well below those that would cause cellular damage. Thus, the device disclosed herein is a safe and effective treatment for a number of women's health indications with a unique method of delivery and mechanism of action.

Example 4

A method for treating urinary stress incontinence in a subject includes the following treatment protocol, and is also outlined in FIG. 4:

A subject is placed on an examination table in a dorsal lithotomy position. The vagina, perineum, and peri-anal area will be cleansed using a sterile saline wipe. Coupling fluid will be applied to the entire treatment area and the treatment tip to ensure safe RF transfer and cooling effectiveness. The coupling fluid acts as a conductor and skin protectant and is not a lubricant. No substitutes should be used for the coupling fluid and no lubricants should be used for the procedure. Additional coupling fluid will be reapplied throughout the treatment to ensure appropriate transfer of RF energy.

A subject is treated with an active treatment tip (delivering 90 J/cm2 of RF energy).

The treatment area is divided into quadrants of the vaginal introitus with the area directly beneath the urethra excluded. One treatment tip per subject will used to administer the protocol.

Position 1: 0-2 cm beyond hymenal ring (100 pulses). The treatment tip placement is beyond hymenal ring: proximal edge 0 cm, distal edge 2 cm. The first set of 100 pulses is applied to the area just behind the hymenal ring using the quadrant approach. Each quadrant is treated with 5 consecutive passes of 5 locations of pulses for a total of 25 pulses/quadrant. Pulses are applied in a clockwise fashion with an overlap of ~0.5 cm. Once a quadrant was fully treated with 25 pulses, the next quadrant will be treated, until all 4 quadrants are treated. The treatment area should avoid the area overlying the urethra, by using the urethral sparing window and avoiding treatment between 11 o'clock and 1 o'clock.

Position 2: 1-3 cm beyond hymenal ring (10 pulses). The treatment tip placement is beyond hymenal ring: proximal edge 1 cm, distal edge 3 cm. The second depth of treatment involves positioning the proximal edge of the treatment tip window ~1 cm behind the hymenal ring. Five pulses are applied directly to the right of the urethra and five pulses are applied directly to the left of the urethra observing the urethral sparing window between 11 o'clock and 1 o'clock.

Position 3: 1-3 cm beyond hymenal ring (100 pulses), Position 3 is ~1 cm overlapped with Position 1. The treatment tip placement beyond hymenal ring: proximal edge 1 cm, distal edge 3 cm (there should be ~1 cm overlap between Position 1 and Position 3). The third set (Position 3) of pulses (which comprises 100 pulses) are applied in a similar fashion to Position 1, but at ~1 cm deeper than Position 1. This provides an ~1 cm overlap of treatment pulses. The treatment area should avoid the area overlying the urethra, by using the urethral sparing window and avoiding treatment between 11 o'clock and 1 o'clock.

Position 4: 2-4 cm beyond hymenal ring (10 pulses), Position 4 is ~1 cm overlapped with Position 2. The treatment tip placement is beyond hymenal ring: proximal edge 2 cm, distal edge 4 cm (there should be ~1 cm overlap between Position 2 and Position 4). The fourth depth of treatment (Position 4) is applied in a similar fashion to the Position 2, but with the proximal edge of the treatment tip window positioned ~2 cm behind the hymenal ring. Five pulses are applied directly to the right of the urethra and five pulses are applied directly to the left of the urethra observing the urethral sparing window between 11 o'clock and 1 o'clock.

The treatment is completed when a total of 220 pulses have been applied.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. Moreover, features described in connection with one embodiment of the invention may be used in conjunction with other embodiments, even if not explicitly stated above. It is therefore to be understood that, within the scope of the claims and their equivalents, the invention may be practiced otherwise than as specifically described.

We claim:

1. A method for treating urinary stress incontinence in a subject, the method comprising:
   non-invasively delivering energy to one or more submucosal regions of a vaginal tissue, thereby heating the one or more submucosal regions to a predetermined temperature; and
   remodeling the one or more submucosal regions of the vaginal tissue of the subject to treat the subject for urinary stress incontinence,
   wherein the one or more submucosal regions are located within 4 predetermined quadrants around a vaginal canal,
   wherein the one or more submucosal regions comprise 20 target tissue locations, such that each of the 4 predetermined quadrants comprises 5 target tissue locations,
   wherein non-invasively delivering energy comprises executing at least 10 energy delivery passes in each of the 4 predetermined quadrants,
   wherein each of the at least 10 energy delivery passes comprises applying, in a predetermined order, 1 to 5 energy pulses to each of the 5 target tissue locations in each of the 4 predetermined quadrants, and
   wherein non-invasively delivering energy comprises delivering at least 20 energy pulses to two or more submucosal regions of a vaginal tissue that is located alongside a urethra of the subject.

2. The method of claim 1, wherein executing at least 10 energy delivery passes in each of the 4 predetermined quadrants comprises:
   executing a first series of 5 energy delivery passes in each of the 4 predetermined quadrants; and
   executing a second series of 5 energy delivery passes in each of the 4 predetermined quadrants,
   wherein the first series of 5 energy delivery passes in each quadrant is completed before the second series of 5 energy delivery passes in each of the 4 predetermined quadrants is initiated, and
   wherein each of the first series of 5 energy delivery passes and the second series of 5 energy delivery passes comprises applying in a predetermined order 1 energy pulse to each of the 5 target tissue locations in each of the 4 predetermined quadrants.

3. The method of claim 2, wherein delivering up to 20 energy pulses to two or more submucosal regions located alongside the urethra of the subject comprises:
   delivering a first series of 10 energy pulses to the two or more submucosal regions located alongside the urethra; and
   delivering a second series of 10 energy pulses to the two or more submucosal regions located alongside the urethra,
   wherein the first series of 10 or more pulses is delivered after executing the first series of up to 5 energy delivery passes in each of the 4 predetermined quadrants, and
   wherein the second series of 10 or more pulses is delivered after executing the second series of up to 5 energy delivery passes in each of the 4 predetermined quadrants.

4. The method of claim 2, wherein executing each energy delivery pass of the first series of 5 energy delivery passes in each of the 4 predetermined quadrants comprises applying, in a predetermined order, 1 energy pulse to each of a first set of 5 target tissue locations in each of the 4 predetermined quadrants such that each target tissue location of the first set of 5 target tissue locations at least partially overlaps with an adjacent target tissue location, and
   wherein executing each energy delivery pass of the second series of 5 energy delivery passes in each of the 4 predetermined quadrants comprises applying in a predetermined order 1 energy pulse to each of a second set of 5 target tissue locations in each of the 4 predetermined quadrants, such that each target tissue location of the second set of 5 target tissue locations at least partially overlaps with an adjacent target tissue location.

5. The method of claim 4, wherein each target tissue location of the second set of 5 target tissue locations in each of the 4 predetermined quadrants is proximal to each target tissue location of the first set of 5 target tissue locations in each of the 4 predetermined quadrants.

6. The method of claim 3, wherein the first series of 10 energy pulses and the second series of 10 energy pulses are delivered to two submucosal regions,
   wherein a first submucosal region of the two submucosal regions is located within a target tissue located on a first side of the urethra,
   wherein a second submucosal region of the two submucosal regions is located within a target tissue located on a second side of the urethra, and
   wherein each energy pulse of the first series of 10 energy pulses and the second series of 10 energy pulses is applied in an alternating manner to the first submucosal region and to the second submucosal region such that two or more energy pulses are not applied in a consecutive manner to a same submucosal region.

7. The method of claim 2, wherein executing the first series of 5 energy delivery passes in each of the 4 predetermined quadrants comprises:
   executing 5 energy delivery passes in a first quadrant;
   executing 5 energy delivery passes in a second quadrant after executing 5 energy delivery passes in the first quadrant;
   executing 5 energy delivery passes in a third quadrant after executing 5 energy delivery passes in the second quadrant; and
   executing 5 energy delivery passes in a fourth quadrant after executing 5 energy delivery passes in the third quadrant.

8. The method of claim 1, wherein remodeling the one or more submucosal regions comprises changing a structural organization and/or biomechanical property of an existing collagen molecule, strengthening or bolstering a collagen-rich site in the one or more submucosal regions, releasing one or more heat shock proteins or other cellular cascades in the one or more submucosal regions, stimulating cellular production and/or deposition of collagen into an extracellular space, or any combination thereof.

9. The method of claim 1, wherein the 4 predetermined quadrants comprise a first quadrant from a 12 o'clock position to a 3 o'clock position, a second quadrant from the 3 o'clock position to a 6 o'clock position, a third quadrant is from the 6 o'clock position to a 9 o'clock position, and a fourth quadrant is from the 9 o'clock position to the 12 o'clock position, and wherein the urethra of the subject is located at the 12 o'clock position.

10. The method of claim 1, wherein the predetermined temperature is between 38° C. to 46° C.

11. The method of claim 1, wherein the predetermined temperature is between 40° to 46° C.

12. The method of claim 1, wherein the predetermined temperature is between 40° to 42° C.

13. The method of claim 1, wherein non-invasively delivering energy comprises applying radiofrequency energy.

14. The method of claim 1, wherein non-invasively delivering energy comprises applying microwave energy.

15. The method of claim 1, wherein non-invasively delivering energy comprises applying ultrasound energy.

16. The method of claim 1, wherein the non-invasively delivering energy is controlled by a feedback control mechanism, such that the predetermined temperature is not exceeded.

17. The method of claim 16, wherein the feedback control mechanism is provided by one or more thermal sensors.

18. The method of claim 16, wherein the feedback control mechanism is provided by one or more impedance monitors.

19. The method of claim 1, further comprising cooling an epithelial tissue layer above the one or more submucosal regions.

20. The method of claim 19, wherein the epithelial tissue layer is cooled to a temperature that ranges from 0° to 10° C.

21. The method of claim 19, wherein the cooling precedes the heating, and continues during the non-invasively delivering energy.

22. The method of claim 19, wherein the cooling occurs during the heating, and continues after the non-invasively delivering energy.

23. The method of claim 22, wherein the combination of cooling and non-invasively delivering energy creates a reverse thermal gradient from a surface layer to the one or more submucosal regions.

24. The method of claim 1, wherein the non-invasively delivering energy does not substantially modify a mucosal epithelium of the vaginal tissue.

25. The method of claim 1, further comprising altering a conformation of the vaginal tissue.

26. The method of claim 1, wherein at least some of the remodeling occurs during the step of non-invasive energy delivery.

27. The method of claim 1, wherein at least some of the remodeling occurs after the step of non-invasive energy delivery.

* * * * *